US011523906B2

(12) United States Patent
Inouye et al.

(10) Patent No.: US 11,523,906 B2
(45) Date of Patent: Dec. 13, 2022

(54) DETACHABLE SLIDING ACTUATORS FOR VALVE REPAIR DEVICES

(71) Applicant: Boston Scientific Scimed, Inc., Maple Grove, MN (US)

(72) Inventors: Joshua M. Inouye, Maple Grove, MN (US); James M. Anderson, Corcoran, MN (US); Graham Krumpelmann, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3 days.

(21) Appl. No.: 16/916,691

(22) Filed: Jun. 30, 2020

(65) Prior Publication Data

US 2021/0000600 A1  Jan. 7, 2021

Related U.S. Application Data

(60) Provisional application No. 62/869,227, filed on Jul. 1, 2019.

(51) Int. Cl.
*A61F 2/24* (2006.01)
(52) U.S. Cl.
CPC .... *A61F 2/2466* (2013.01); *A61F 2220/0041* (2013.01); *A61F 2250/001* (2013.01)
(58) Field of Classification Search
CPC .......... A61F 2/24; A61F 2/2418; A61F 2/243; A61F 2/2442; A61F 2/2466; A61F 2220/0041
See application file for complete search history.

(56) References Cited

U.S. PATENT DOCUMENTS

| | | | |
|---|---|---|---|
| 9,610,156 B2 | 4/2017 | Lashinski | |
| 9,615,926 B2 * | 4/2017 | Lashinski | ............. A61F 2/2463 |
| 9,622,862 B2 | 4/2017 | Lashinski et al. | |
| 9,848,983 B2 | 12/2017 | Lashinski et al. | |
| 10,335,275 B2 | 7/2019 | Lashinski et al. | |
| 10,548,731 B2 | 2/2020 | Lashinski et al. | |
| 10,555,813 B2 | 2/2020 | Lashinski et al. | |
| 2017/0135816 A1 | 5/2017 | Lashinski et al. | |

FOREIGN PATENT DOCUMENTS

| | | |
|---|---|---|
| WO | 2006105084 A2 | 10/2006 |
| WO | 2013126529 A2 | 8/2013 |
| WO | 2016118786 A1 | 7/2016 |

OTHER PUBLICATIONS

International Search Report and Written Opinion for the International Patent Application No. PCT/US2020/040274, dated Sep. 24, 2020, 12 pages.

* cited by examiner

*Primary Examiner* — William H Matthews
(74) *Attorney, Agent, or Firm* — Seager, Tufte & Wickhem LLP

(57) ABSTRACT

Various embodiments of an implant delivery systems including at least one removable actuator to reshape a valve annulus are described. The systems may use the removable actuator to customize annular reshaping at a treatment site and withdraw the actuator from the treatment site following custom reshaping to provide a low profile annuloplasty implant.

15 Claims, 20 Drawing Sheets

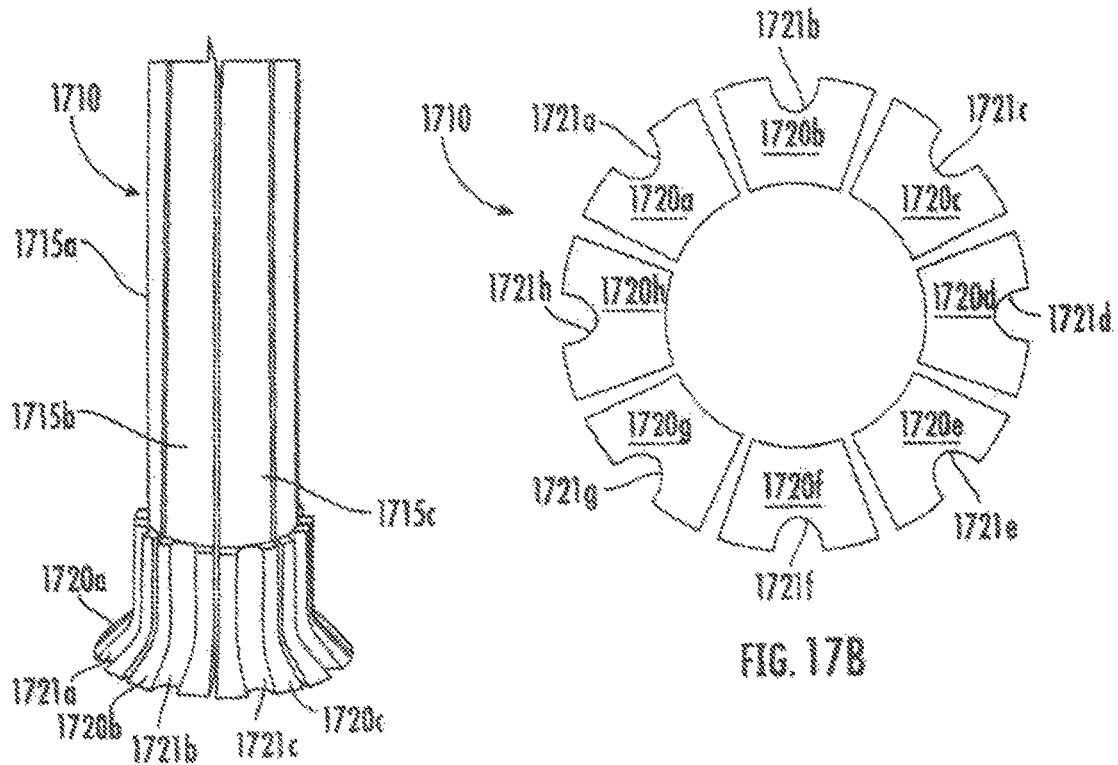
FIG. 17A
FIG. 17B
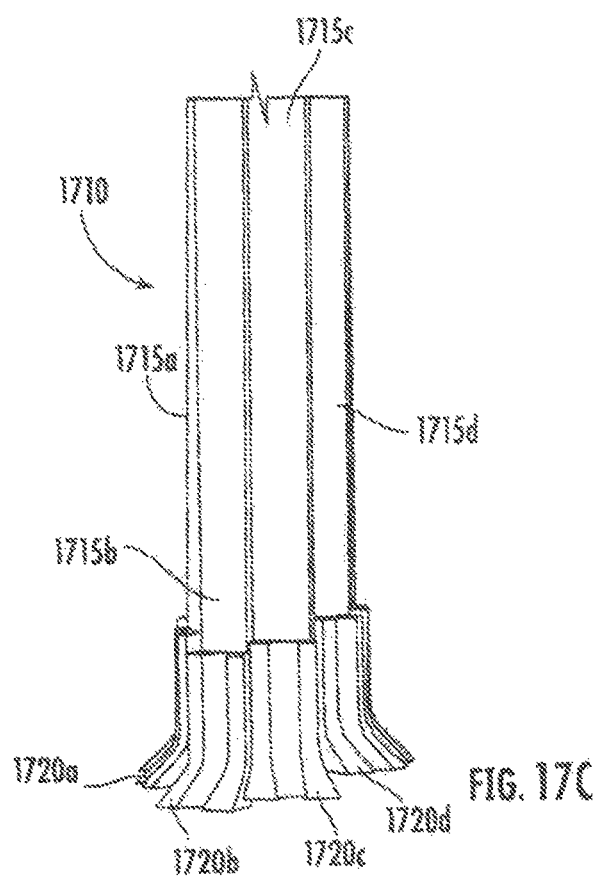
FIG. 17C

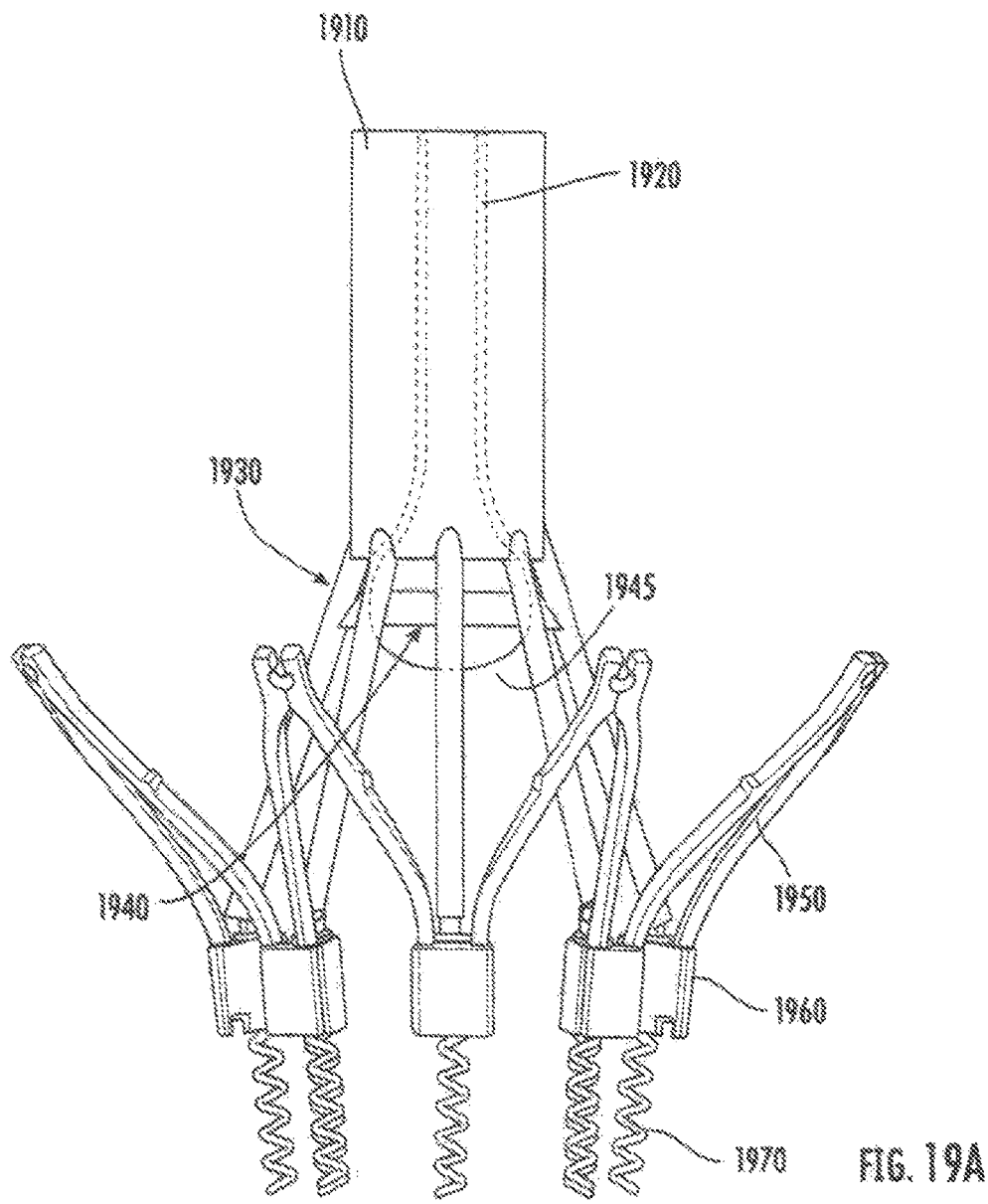

DETACHABLE SLIDING ACTUATORS FOR VALVE REPAIR DEVICES

CROSS-REFERENCE TO RELATED APPLICATIONS

The present application claims the benefit of priority under 35 U.S.C. § 119 to U.S. Provisional Patent Application 62/869,227, filed Jul. 1, 2019, which application is incorporated herein by reference in its entirety for all purposes.

FIELD

The present disclosure relates generally to the field of implantable medical devices and more particularly to implantable devices, systems and methods for adjusting heart features.

BACKGROUND

The mitral valve lies between the left atrium and the left ventricle of the heart. The mitral valve includes two leaflets, an anterior leaflet and a posterior leaflet, which coapt during systolic contraction. The mitral annulus is a saddle shaped fibrous ring that surrounds the mitral valve and supports the valve's leaflets. In a healthy heart blood flows through an open mitral valve during diastole with contraction of the left atrium and mitral valve leaflets close during systole with contraction of the left ventricle.

Mitral insufficiency (MI) (also referred to as mitral regurgitation or mitral incompetence) is a form of heart disease where the mitral annulus dilates excessively and the valve leaflets no longer effectively close, or coapt, during systolic contraction. Consequently, regurgitation of blood occurs during ventricular contraction and cardiac output decreases.

The goal of mitral valve annuloplasty is to regain mitral valve competence by restoring the physiological form and function of the normal mitral valve apparatus, including one or more of the mitral valves and the mitral annulus. Some endoluminal mitral valve annuloplasty techniques use a deployment catheter and transluminal navigation to deliver an implant to a mitral valve treatment site.

While endoluminal annuloplasty techniques are less invasive than open heart annuloplasty techniques, cardiac implants are not without risk. For example, devices attached within a heart are subject to the stresses and strains associated with palpitation of the cardiac muscle. It is with these considerations in mind that the improvements of the present disclosure may be useful.

SUMMARY

Embodiments of the present disclosure relate to a system and method for deploying a low profile valve annulus implant, for example for use in reshaping a heart valve annulus. According to one aspect, an implant delivery system includes a frame having a proximal end, a distal end and adjacent struts joined at a proximal apex. The system includes an actuator, removably coupled to the frame and comprising one or more axially translatable adjustment components configured to one of expand or contract the frame.

In some embodiments, the one or more axially translatable adjustment components of the actuator may include a shaft comprising a distal shaft end comprising a shaft head, the shaft head positioned within an opening of the proximal apex of the frame and a collar disposed over at least a portion of the shaft including the shaft head to retain the shaft head within the opening of the proximal apex, the collar configured to travel distally along the shaft and over the proximal apex of the frame to engage the adjacent struts in response to a first activation of the shaft. The collar may be configured to travel proximally along the shaft in response to a second activation of the shaft to release the shaft head from the proximal end of the frame.

The shaft may include a proximal shaft end comprising a drive coupler and shaft engagement features disposed along a portion of an engagement portion of the shaft disposed between the drive coupler and the shaft head. The collar may include a proximal end, a distal end, and a bore extending therethrough, the bore comprising bore engagement features disposed on at least a portion of an inner surface of the bore, the shaft engagement features configured to engage with the bore engagement features to translate the collar along the shaft. In some embodiments, a length of the engagement portion of the shaft may be at least equal to a length of the collar. In some embodiments, at least one of the shaft engagement features or the bore engagement features include one or more threads and one of the first activation or the second activation of the shaft includes rotation of the shaft. In some embodiments, the frame may include a second plurality of struts joined at a distal apex that supports an anchor housing, the anchor housing comprising a cinch lumen extending therethrough configured to slidably accept a cinch cord.

In some embodiments, the adjacent struts of the frame include a biased configuration, and the collar includes a spreading mechanism configured to urge the adjacent struts against returning to the biased configuration. The spreading mechanism may include at least one arm configured to engage at least one strut of the adjacent struts to urge the at least one strut against returning to the biased configuration.

In some embodiments, release of the shaft head from the proximal apex releases the spreading mechanism from between the adjacent struts to return the adjacent struts to the biased configuration.

In other embodiments, the frame may include a plurality of distal apices and a plurality of anchor housings may be disposed on at least a subset of the plurality of distal apices, each anchor housing supporting an anchor, and the actuator may include a sleeve, a plurality of cantilevered tubes disposed within the sleeve and coupled at proximal ends to a distal portion of the sleeve, a plurality of drive shafts, each drive shaft translatably disposed within one of the plurality of cantilevered tubes and configured to extend beyond the distal end of an associated cantilevered tube to drive one of the anchors, a core disposed within the sleeve such that the plurality of cantilevered tubes slideably engage an outer surface of the core, the core disposed to translate axially within the sleeve, wherein each cantilevered tube includes a flex portion. In such embodiments, axial translation of the core causes the cantilevered tubes to rotate at the flex portion to vary an angular deflection of the distal end of the cantilevered tube to expand the distal apices of the frame.

In some embodiments, the core may include a plurality of arms arranged circumferentially within the sleeve, and wherein the plurality of arms is independently translatable within the sleeve to independently control the angular deflection of a respective cantilevered tube. In some embodiments, each drive shaft may be axially translatable beyond a distal end of an associated cantilevered tube to control a configuration of the frame.

In some embodiments, an inflatable device may be disposed within a central lumen of the core and configured to control an angular deflection of the plurality of cantilevered tubes. In some embodiments, the core may include a plurality of detents, each detent for slidably supporting one of the plurality of cantilevered tubes.

According to another aspect, a system includes a frame having a proximal end, a distal end and adjacent struts joined at a plurality of distal apices and a plurality of proximal apices. The system includes a plurality of anchors supported by the distal apices of the frame and an actuator, removably coupled to the frame and comprising one or more axially translatable adjustment components configured for one of expansion or contraction of the frame. The axially translatable adjustment components may be configured for removal through the catheter following affixation of the frame by the plurality of anchors to annular tissue.

In some embodiments, the one or more axially translatable adjustment components may include a shaft comprising a distal shaft end comprising a shaft head, the shaft head positioned within an opening of a proximal apex of the frame and a collar disposed over at least a portion of the shaft including the shaft head to retain the shaft head within the opening of the proximal apex, the collar configured to travel distally along the shaft and over a proximal apex of one of the plurality of proximal apices of the frame to engage the adjacent struts to one of expand or compress the frame in response to a first activation of the shaft, and the collar may be configured to travel proximally along the shaft in response to a second activation of the shaft to release the shaft head from the proximal apex of the frame.

In some embodiments, the system may include a plurality of anchor housings disposed on at least a subset of the plurality of distal apices, each anchor housing supporting an anchor of the plurality of anchors. The one or more axially translatable adjustment components of the actuator may include a sleeve, a plurality of cantilevered tubes disposed within the sleeve and coupled at proximal ends to a distal portion of the sleeve, a plurality of drive shafts, each drive shaft translatably disposed within one of the plurality of cantilevered tubes and configured to extend beyond the distal end of an associated cantilevered tube to drive one of the anchors, a core disposed within the sleeve such that the plurality of cantilevered tubes slideably engage an outer surface of the core, the core disposed to translate axially within the sleeve, wherein each cantilevered tube includes a flex portion, and wherein axial translation of the core causes the cantilevered tubes to rotate at the flex portion to vary an angular deflection of the distal end of the cantilevered tube to expand the distal apices of the frame.

According to another aspect, a method for deploying an implant delivery system to a valve annulus repair site includes the steps of transluminally delivering a distal end of a catheter comprising implant components to the valve annulus repair site. In some embodiments, the implant delivery system may include a frame including a first plurality of struts joined at a plurality of apices, and an actuator, coupled to the frame and comprising one or more axially translatable adjustment components. The method includes releasing the frame from the catheter, adjusting a shape of the frame by axially translating the axially translatable adjustment components to expand or contract the frame, anchoring the frame to the valve annulus repair site and releasing the actuator from the frame.

In some embodiments, the implant delivery system may include a plurality of collars, each collar disposed on one of the plurality of apices of the frame, where the step of adjusting the shape of the frame includes translating the collars along the plurality of apices of the frame and the step of releasing the actuator from the frame includes the step of removing the collars from the plurality of apices of the frame.

In other embodiments, the implant delivery system may further include a sleeve, a plurality of cantilevered tubes disposed within the sleeve, a plurality of drive shafts, each drive shaft translatably disposed within one of the plurality of cantilevered tubes and coupled to the frame, and a core shaft extending through the sleeve, and the step of adjusting the shape of the frame includes the steps of axially translating the core shaft within the sleeve to vary an angular deflection of the distal end of the cantilevered tube.

With such an arrangement, a low-profile valve annulus implant with increased flexibility and reduced potential for migration, fracture, thrombus and embolic risk is provided.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 17A-17C illustrate various views of a core device with independently controlled arms as disclosed herein;

FIGS. 19A and 19B illustrate an alternate embodiment of an implant delivery system as disclosed herein including an inflatable actuation mechanism.

DETAILED DESCRIPTION

Figure 1:
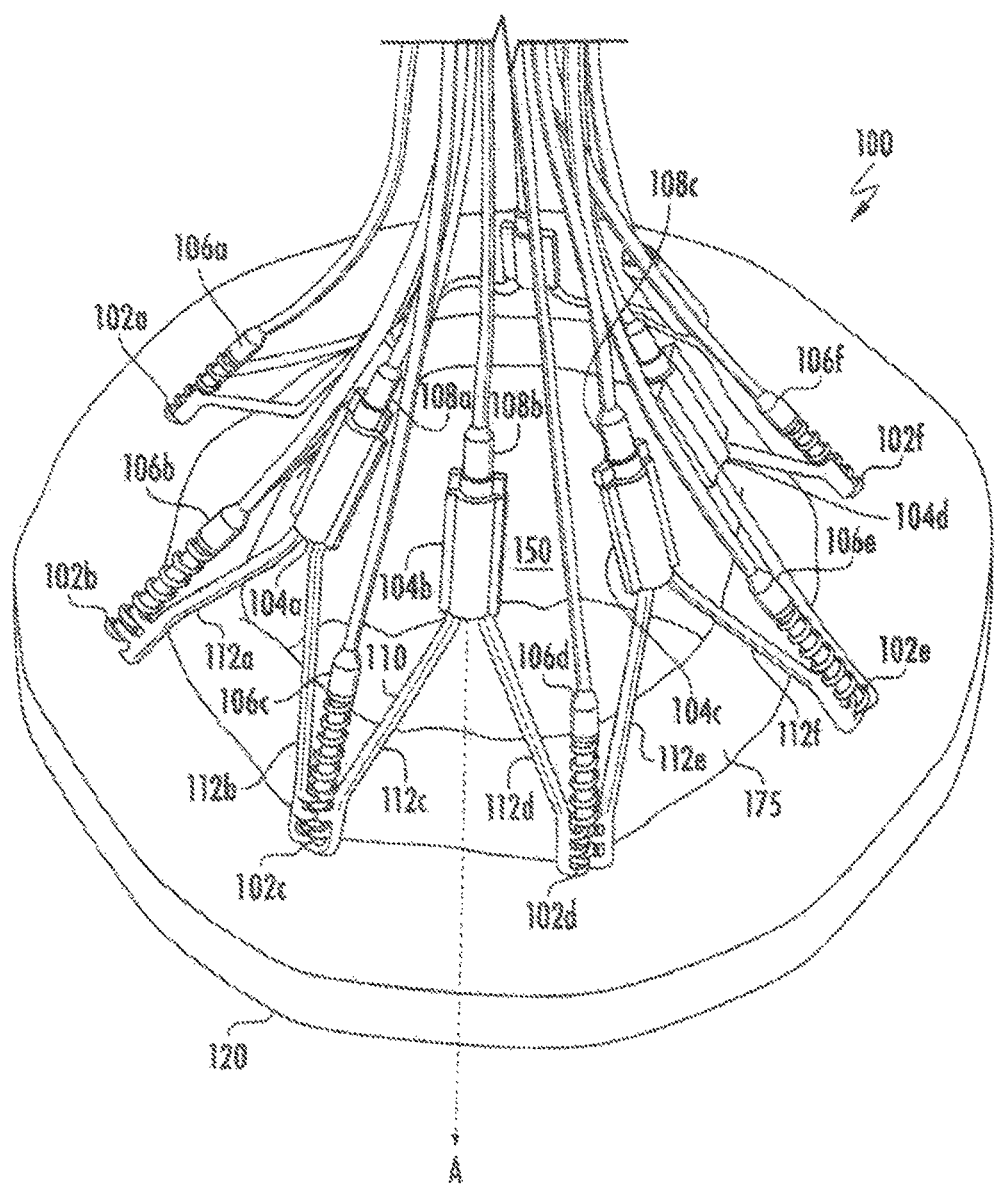
FIG. 1 illustrates one embodiment of a prior art reconstructive valve annulus implant.

Valve annuloplasty implants may include independently controlled actuators that enable custom reshaping of the valve annulus during deployment. FIG. 1 illustrates an atrium 120 where one such prior art implant 100 has been deployed around a cardiac valve 150 such that a plurality of anchors 102a-102f of the implant are positioned for engagement with a valve annulus 175. The implant 100 includes a generally tubular frame 110 formed from a plurality of struts 112a-112f joined at a proximal end by the collars 104a-104d, and at distal ends by anchors 102a-102f. Anchors 102a-102f may each be coupled to anchor drivers 106a-106f. In one embodiment, anchor drivers are configured to rotate anchors 102a-102f to drive the anchors into the tissue proximate to the valve annulus 175 during an anchoring step of implant deployment. In one embodiment, collars may be configured for distal advancement over the struts. For example, collar 104b may translate along an axis A in FIG. 1. In some embodiments, "axial" as applied to axial movement or restraint of the collars includes directions that are at least partially in the proximal or distal direction and that are parallel or generally parallel to a central axis extending through (e.g. proximally-distally) the frame.

As shown in FIG. 1, struts 112c, 112d may extend away from the proximal apex supporting collar 104b in opposing directions. Distal advancement of the collar 104b over struts 112c, 112d pulls the struts 112c, 112d together within the collar 104b, and as a result reduces the distance between anchors 102c and 102d to reshape the annulus 175. Collars 104a-104d may be independently actuated in accordance with a reshaping objective for each anchor pair. Once each collar has been actuated, in one embodiment the drive cables may be released from actuator drivers 108a, 108b, 108c.

Figure 2:
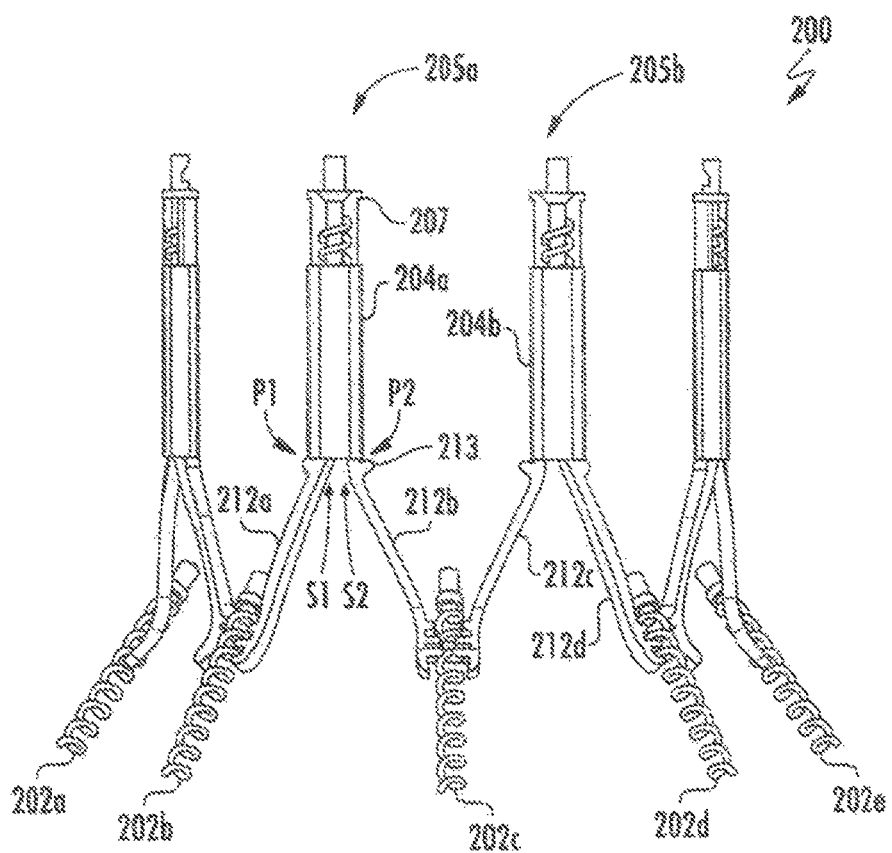
FIG. 2 is a detailed diagram of a portion of the prior art reconstructive valve annulus implant of FIG. 1.

FIG. 2 illustrates a portion of a prior art implant 200, such as implant 100 of FIG. 1, post deployment. Collar 204a has been distally advanced along struts 212a, 212b, for example, as a result of activation of shaft 205a, to draw together anchors 202b and 202c. Collar 204b has been distally advance along struts 212c, 212d by activation of shaft 205b to draw together anchors 202c and 202d. According to one aspect, struts may include features configured to limit the translation of the collar along the struts. For example, strut 212b is shown to include a flange 213 positioned to limit the distal translation of the collar 204a along strut 212b, and a lip 207 disposed on a proximal end of strut 212b, to limit proximal translation of the collar 204a.

The prior art devices of FIGS. 1 and 2 enable a less invasive, anatomy preserving, valve readjustment solution with patient specific customization. However, over time the chronic contact between struts 212a, 212b and the rigid collar 204a may produce high strain regions on the struts, increasing the potential for material fatigue and fracture. For example, as collar 204a is slid down over struts 212a, 212b, pressure from the collar may be transferred to point P1 of strut 212a, resulting in high strain at point S1. Likewise, pressure at pinch point P2 results in high strain at point S2 of strut 212b. Over time, the regions of high strain may become fatigued and fracture, reducing the efficacy of the implant.

In addition to device fatigue, according to one aspect it is realized that it would be desirable to reduce an implant profile to minimize the potential for inadvertent contact between the implant and the cardiac wall. Further, it would be desirable to minimize the presence of threads or other features of an implant, such as screws, etc., which may result in thrombus formation.

According to one aspect, an improved implant design, system and method of deployment overcome these problems by removing at least a portion of the implant following anchoring and actuation. With such an arrangement, the advantages of annular customization may be realized without the associated risks.

According to one embodiment, removal of at least a portion of the implant may be achieved through the introduction of an implant including a removable actuator. In one embodiment, the removable actuator may include a shaft, supported by an apex of a frame, and a collar translationally disposed over at least a portion of the shaft. The collar may be configured to travel distally along the shaft and over the proximal apex of the frame to engage adjacent struts of the proximal apex to reduce spacing between anchors. According to one aspect, the implant may include a cinching mechanism to retain the frame in the actuated configuration. Once actuated and retained, the collar may be configured to travel proximally along the shaft to expose the shaft for release from the frame. In one embodiment, the collar may include a lock mechanism to secure the shaft within the collar for removal. Removing both the collar and the shaft provides several advantages. For example, removing the collar and shaft provides a lower profile implant that minimizes the potential for inadvertent contact with the cardiac wall. Removing the shaft reduces threads and other features and thereby minimizes thrombus risk. Removing the collar relieves stress on the frame, reducing fracture risk. In addition, removing the presence of collars in the annular implant allows for use of a lighter weight, less robust frame material because the frame need not be designed to withstand fracture forces during chronic use.

These and other beneficial aspects of the disclosed implant are described in more detail below. It should be noted that, although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage or other similar heart failure conditions.

As used herein, the term "distal" refers to the end farthest away from the medical professional when introducing a medical device into a patient, while the term "proximal" refers to the end closest to the medical professional when introducing a medical device into a patient.

Figure 3A:
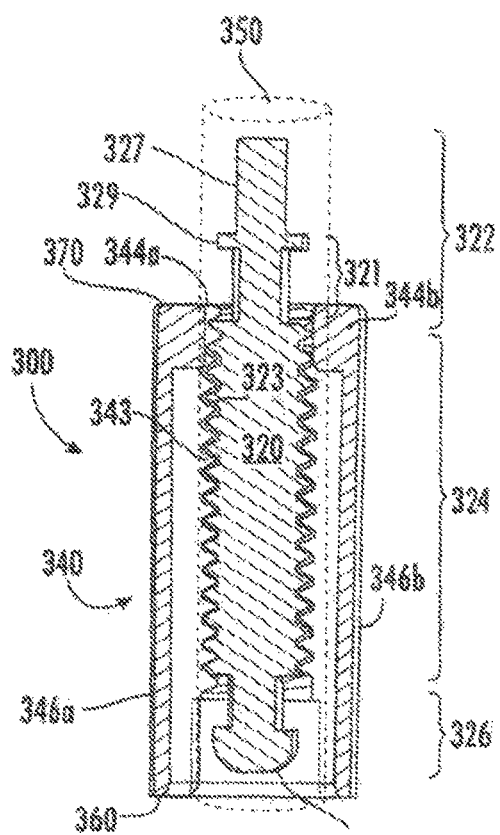
FIGS. 3A-3D are perspective views of an exemplary actuator in accordance with an embodiment of the present disclosure.

FIGS. 3A-3D illustrate one embodiment of an actuator 300 of this disclosure in a variety of views and configurations. FIG. 3A is a cross section view of an actuator 300 taken along line 3A-3A of FIG. 3B. In FIG. 3A, the actuator 300 is shown to include a shaft 320 disposed within a bore 350 of a collar 340. In one embodiment, the collar 340 is an axially translatable adjustment component configured to control one of expansion and/or contraction of an implant frame. The shaft is shown to include a proximal end 322, an engagement portion 324 and a distal end 326. In one embodiment, a shaft head 325 may be disposed at a distal end 326 of shaft 320 and carried by a portion of the frame over which the collar 340 translates. For example, the frame may define a window or other opening for carrying the shaft head, such that the shaft 320 may be freely or substantially freely rotatable about its rotation axis within the opening but is constrained or substantially constrained against axial movement and/or release from the frame.

In some embodiments the shaft 320 includes an elongated structural member extending through a central axis of the bore 350. The shaft 320 may include a threaded shaft including one or more threads and may be rotated internally to the collar 340. Rotational forces upon the shaft 320 may be transmitted from external engagement features, such as external threads 323, of the shaft 320 to corresponding internal features, such as teeth or internal threads 343, of the collar 340, to cause axial movement of the collar 340. It should be noted that external threads 323 may be included on only a portion of shaft 320. For example, in FIG. 3A, the threads within the length of 324 may only be provided on the bottom half or one-third of the threaded portion as shown to achieve the same functionality. The upper half or two-thirds may be simply circular without threads, or at or below the minor diameter of the threads.

According to one aspect the length of the engagement portion, for example the length of the portion of the shaft comprising external threads 323, may be at least equal to the length of the collar 340 to ensure that the collar 340 is able to translate proximally over the shaft 320 to expose the shaft head 325 for release.

In some embodiments, the shaft 320 may be cylindrical. In other embodiments, the shaft 320 may have other shapes, or be partially cylindrical, etc. The width of the shaft 320 may be constant along all or a portion of the shaft. In some embodiments, the width may vary along all or a portion of the shaft. The shaft 320 may be solid, hollow, partially solid, or partially hollow. The shaft 320 may be formed of stainless steel, cobalt-chromium, titanium, other implant grade materials, polymers, plastics, alloys, other suitable materials, or combinations thereof.

The external threads 323 of shaft 320 may have a variety of different pitches and inner/outer diameters. The shaft 320 may have one or more portions having external threads 323 measuring from about 0.010 to about 0.090 inches in diameter, from about 0.020 to about 0.080 inches in diameter, from about 0.030 to about 0.070 inches in diameter, or from about 0.040 to about 0.060 inches in diameter, or other amounts or ranges. This diameter may be an outer diameter as measured from peak to opposite peak of the threads 323. The shaft 320 may have from about 10 to about 150 threads per inch, from about 20 to about 140 threads per inch, from about 30 to about 130 threads per inch, from about 40 to about 120 threads per inch, from about 50 to about 130 threads per inch, from about 60 to about 120 threads per inch, from about 70 to about 110 threads per inch, from about 80 to about 100 threads per inch, or other amounts or ranges. In some embodiments, the shaft may include a portion having an external thread measuring from about 0.040 to about 0.060 inches in diameter and from about 60 to about 120 threads per inch. The pitch and inner/outer diameters of the threads may complement that of corresponding internal threads 343 of the collar 340.

The shaft 320 may further include a drive coupler 327 and a neck 321 formed integrally with or coupled to a proximal end 322 of the shaft. In one embodiment, neck 321 includes a portion of the shaft 320 having a reduced diameter. In one embodiment, a flange 329 extends radially beyond the neck 321 and is positioned proximally to the neck 321. In some embodiments, the flange 329 may be configured to limit the extend of proximal travel of the collar over the shaft.

The collar 340 includes the bore 350 extending from a proximal end 370 to the distal end 360. As described above, the bore 350 may include internal threads 343 or other features disposed on an internal wall of bore 350 that cooperate with external threads 323 of the shaft 320 to translate the collar 340 over the shaft 320 when the shaft is driven. For example, internal threads 343 may be a complementary, continuous or non-continuous helical pattern of threads or other features configured to slidably and/or rotatably engage some or all of the external threads 323 of the shaft 320.

The collar 340 may also include features that cooperate with the shaft to limit travel of the collar 320 and/or lock the collar to the shaft. Such features may include a pair of arms 346a, 346b which may be inwardly biased towards a central axis of the bore 350 in a relaxed, biased configuration. The arms 346a, 346b may be fixed at a distal end within the bore 350 of the collar, and/or may be integrally formed with the collar at the distal end. The arms Tabs 344a, 344b, coupled to distal ends of the arms 346a, 346b may be configured to engage the neck 321 when the collar is proximally advanced to align the tab 344a, 344b with neck 321 of the shaft.

The collar 340 and/or features thereof such as the arms 346a, 346b and tabs 344a, 344b may be formed of a shape memory material, such as, for example, a nickel titanium alloy such as Nitinol. In some embodiments, the collar 340 and/or features thereof such as the tabs 344a, 344b may be formed of other materials, such as metals, other metal alloys, plastics, polymers, composites, other suitable materials, or combinations thereof.

Figure 3B:
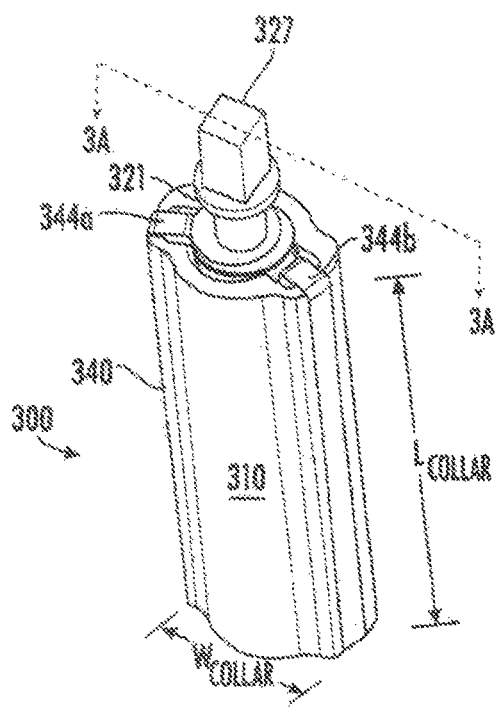

FIG. 3B is a distally facing perspective view of the actuator 300 of FIG. 3A. In one embodiment, the collar may be generally rectangular in shape, having a length $L_{Collar}$ and a width $W_{Collar}$. The collar 340 may include an inward facing surface 310 that is oriented towards a central axis of an implant frame during use. An opposing surface (not shown) may be a surface of the collar 340 that is opposite to the internal surface 310. In the configuration of FIG. 3B, tabs 344a and 344b are shown in an unlocked position, wherein the shaft rides freely within the bore of the collar 340. Neck 321 is shown extending past a proximal end of collar 340.

Figure 3C:
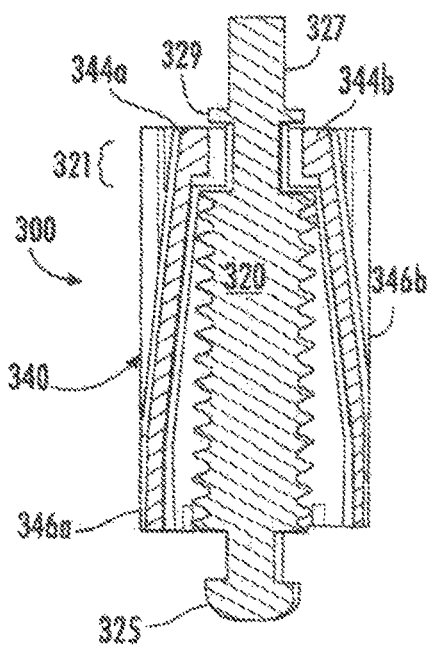
Figure 3D:
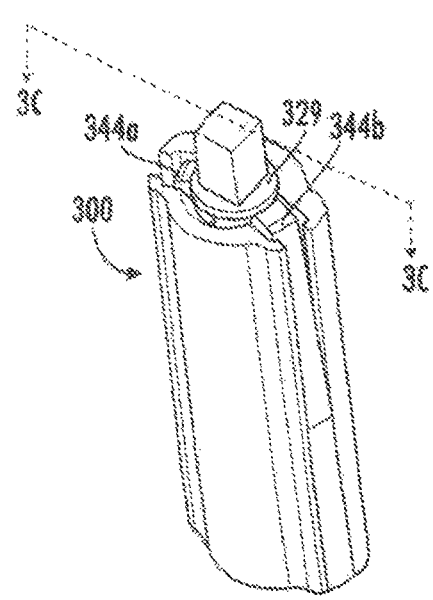

FIG. 3C is a cross section of the actuator 300 in a locked state that secures the shaft 320 within the collar 340 for removal from a valve treatment site, the cross section taken along line 3C-3C of FIG. 3D. In FIG. 3C, collar 340 has been proximally translated to expose shaft head 325, enabling release of the shaft head 325 from an opening of the frame. During proximal advancement of the collar 340 over the shaft 320, as the neck 321 aligns with tabs 344a, 344b, the inward bias of arms 346a, 346b causes tabs 344a, 344b to engage with neck 321. As a result, the proximally facing surfaces of tabs contact distal facing surface of flange 329, limiting further proximal motion of the shaft to effectively lock the shaft to the collar during removal.

FIG. 3D is a distal facing perspective of the actuator 300 of FIG. 3C. In FIG. 3D tabs 344a, 344b can be seen biased inwardly and retained by flange 329. With such an arrangement, threads or other features of the actuator may be encased by the collar during actuator removal, reducing the potential for thrombus and other embolic risks caused by threads and/or sharp edges of the implant.

Removable actuators such as those of FIG. 3A-3D may be advantageously utilized by transluminal implants to customize annulus reshaping while minimizing safety and efficacy risks. It is appreciated that transluminal implants may take many forms; for example, some implants may include shaped memory frames that are biased to assume a compressed configuration, others may include shaped memory frames that are biased to assume an expanded or partially contracted configuration. Still others may use mechanically controlled expansion or contraction techniques.

Various embodiments of removable actuators are described herein. It is understood that the actuators may be incorporated for use in a variety of implant devices, including but not limited to those described, for example, in U.S. patent application Ser. No. 14/861,877 entitled "ADJUSTABLE ENDOLUMENAL IMPLANT FOR RESHAPING MITRAL VALVE ANNULUS and filed on Sep. 22, 2015 (issued on Apr. 11, 2017, as U.S. Pat. No. 9,615,926), as described, for example, in U.S. patent application Ser. No. 15/280,004 entitled "METHODS FOR DELIVERY OF HEART VALVE DEVICES USING INTRAVASCULAR ULTRASOUND IMAGING" and filed on Sep. 29, 2016 (issued on Jul. 2, 2019, as U.S. Pat. No. 10,335,275), as described, for example, in U.S. patent application Ser. No. 15/043,301 entitled "VALVE REPLACEMENT USING ROTATIONAL ANCHORS" and filed on Feb. 12, 2016 (issued on Dec. 26, 2017, as U.S. Pat. No. 9,848,983), as described, for example, in U.S. patent application Ser. No. 15/352,288 entitled "IMPLANTABLE DEVICE AND DELIVERY SYSTEM FOR RESHAPING A HEART VALVE ANNULUS" and filed on Nov. 15, 2016 (issued on Feb. 11, 2020, as U.S. Pat. No. 10,555,813), as described, for example, in U.S. patent application Ser. No. 14/427,909 entitled "MITRAL VALVE INVERSION PROSTHESES" and filed on Mar. 12, 2015 (issued on Apr. 4, 2017, as U.S. Pat. No. 9,610,156), and/or as described, for example, in U.S. patent application Ser. No. 15/893,122 entitled "IMPLANTABLE DEVICE AND DELIVERY SYSTEM FOR RESHAPING A HEART VALVE ANNULUS" and filed on Feb. 16, 2006 (issued on Feb. 4, 2020, as U.S. Pat. No. 10,548,731), the entire disclosure of each of which is incorporated herein by reference for all purposes and forms a part of this specification. Thus, the description of particular features and functionalities herein is not meant to exclude other equivalent features and functionalities such as those described in the incorporated references.

Figure 4A:
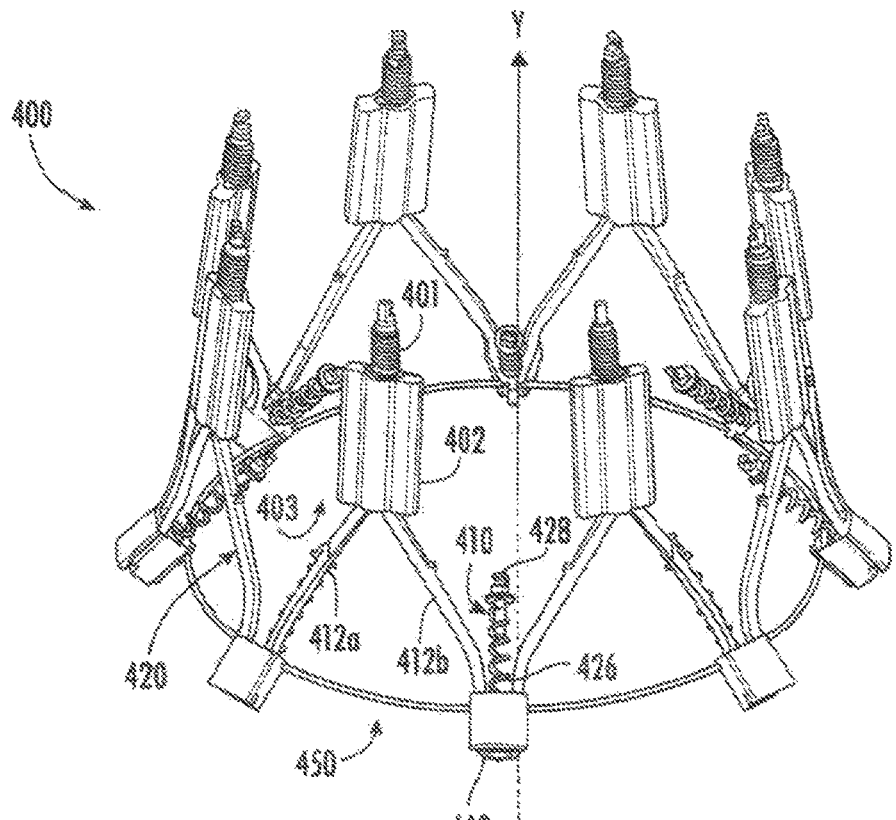
FIGS. 4A and 4B are diagrams of an exemplary implant in accordance with an embodiment of the present disclosure.

FIG. 4A illustrates one embodiment of an implant 400, where for ease of description only a subset of components is numbered. The implant is shown to include a frame 420 that releasably carries actuators such as actuator 403, each actuator 403 including a shaft 401 and a collar 402. The implant 400 is further shown to include a plurality of anchor housings coupled to frame 420, such as anchor housing 440 disposed at a distal end of the frame 420. In one embodiment, the anchor housing 440 may serve multiple purposes, including providing a lumen for passage of an anchor 410 into annular tissue, coupling the frame 420 to the anchor 410 and, as described in more detail later herein, providing a cinch lumen for a cinch cord 450 that may be used to cinch, constrain and/or otherwise adjust and/or retain relative positions of the anchors 410 following or as part of annular reconfiguration.

The frame 420 may extend circumferentially around and partially axially along a central axis Y of the frame 420. The frame 420 may be generally symmetric with respect to the axis Y although it need not be symmetric with respect to the axis Y. The frame 420 may include a generally tubular shape, where herein "tubular" includes circular as well as other rounded or otherwise closed shapes. The frame 420 may be configured to change shape, size and/or configuration. For example, the frame 420 may assume various shapes, sizes, configurations etc. during various phases of deployment such as during pre-delivery, delivery, tissue engagement and cinching.

According to one embodiment, the frame 420 may be formed from one or more struts 412a, 412b that may form all or part of the frame 420, where the struts 412a, 412b may include elongated structural members formed of a metal alloy. The struts 412a, 412b and/or other parts of the frame 420 may be formed of a shape memory material, such as an alloy of nickel titanium. In some embodiments, the struts 412a, 412b and/or other parts of the frame 420 are formed of other metals, metal alloys, plastics, polymers, composites, other suitable materials, or combinations thereof. In FIG. 4A sixteen struts are shown although it is appreciated that in some embodiments, there may be fewer or more than sixteen struts 412a, 412b. In some embodiments, there may be at least two, four, six, eight, ten, twelve, fourteen, eighteen, twenty, twenty-two, twenty-four, twenty-six, twenty-eight, thirty, or more struts. It will be appreciated that the present invention is not limited to an implant having a particular number of struts.

In one embodiment, the struts may be formed from the same, monolithic piece of material (e.g. tube stock). Thus, the struts 412a, 412b may refer to different portions of the same, extensive component. Alternatively, the struts 412a, 412b may be formed separately and attached permanently together, for example by welding or other methods. In some embodiments, the struts 412a, 412b may be separate components that are detachably coupled together by other components of the implant 400. For example, the struts 412a, 412b may be held together via various components described herein, such as collars 402, anchors 410, anchor housings 440, other features, or combinations thereof. In some embodiments, separate struts may include two or more struts permanently attached together such as at an apex, and the separate units may each be coupled together, either permanently or detachably, to form the frame 420. In some embodiments, the struts 412a, 412b may be attached by hinges, pins, or other suitable means.

Struts 412a, 412b may generally have a rectangular cross-section but can vary in circumferential width and radial thickness to allow for different beam characteristics and forces applied as the collars are advanced over the struts. This may facilitate for example post implantation constriction or remodeling of the annulus, as further described below.

The struts 412a, 412b may extend around the axis to form the various shapes of the frame 420. The struts 412a, 412b may be arranged such that the wall pattern of the frame 420 may be approximately sinusoidally or zig-zag shaped. In some embodiments, the wall pattern may have other suitable shapes, sinusoidal or otherwise. The vertices of the sinusoidal shaped frame 420 may be pointed or rounded.

Figure 4B:
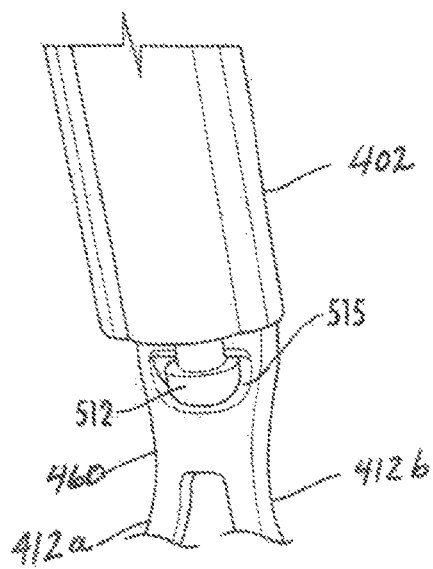

In some embodiments, separate strut units may include two or more struts permanently attached together such as at an apex, and the separate units may each be coupled together, permanently or detachably to form a frame. As shown in FIG. 4B, pairs of adjacent struts 412a, 412b are shown to meet at a proximal apex 450. The terms "apex," "apices," and the like may be used interchangeably with terms "crown," "crowns," and the like, as used herein and as used in any reference incorporated by reference herein, unless otherwise stated. In one embodiment, an 'apex' may include a proximal or distal portion of the frame, for example the portion of the frame including where struts adjoin and/or the portion of the frame along which a collar may travel and/or the portion of the frame that the collar may cover during translation.

A proximal apex 460 may be configured to have a restraint such as the collar 402 fitted over and/or around at least a portion of the proximal apex 450. In the embodiment of FIG. 4B, the exposed proximal apex 460 of the frame is shown to include a proximal apex window 515 configured to releasably carry a shaft head 512. As shown in FIG. 4B, proximal advancement of the collar 402 over the shaft head 512 releases the shaft head 512 from the proximal apex window 515, thereby enabling removal of the collar 402 from the frame.

Referring back to FIG. 4A, the implant 400 may include one or more anchors 410. In some embodiments, the anchors 410 may include a helical portion 426 and a proximal anchor head 428 comprising a drive coupling which may include a hook or other feature to engage a driving tool. The anchors may be made of a suitable biocompatible metal alloy such as stainless steel, cobalt chromium, platinum iridium, nickel titanium, other suitable materials, or combinations thereof. Each anchor 410 may be sharpened at its distal point, or leading turn, so as to facilitate penetration into the cardiac tissue. Each anchor 410 may be from about ten to about fifteen millimeters (mm) in total axial length. In some embodiments, the anchors 410 may be shorter or longer than ten to fifteen millimeters (mm) in total axial length. By "total" axial length it is meant the axial length of the anchor 410 from the end of the distal penetrating tip to the opposite, proximal end of the head 428. The helical portion 426 of the anchor 410 may be from about six to about twelve millimeters (mm) in length in an axial direction. In some embodiments, the helical portion 426 of the anchor may be shorter or longer than six to twelve millimeters (mm) in axial length. The anchor head 428 and/or other non-helical portions of the anchor 410 may be from about three to about four millimeters (mm) in axial length. In some embodiments, the anchor head 428 and/or other non-helical portions may be shorter or longer than three to four millimeters (mm) in axial length. The anchors 410 are capable of extending from about four to about seven millimeters (mm) axially beyond the anchor housing 440. For example, the helical portion 426 of the anchors 410 may extend from four to seven millimeters (mm) into the cardiac tissue. Anchors 410 are shown having a non-parallel angle (e.g., acute or obtuse) relative to axis Y, which may be advantageous for engaging annular tissue and reducing potential for anchor pullout. However, embodiments are not so limited. For example, anchors 410 may be substantially parallel to axis Y, such that anchors 410 extend in a substantially axial direction (e.g., perpendicular) relative to a plan formed a base of each of the anchor housings 440.

FIG. 4A illustrates the implant 400 deployed in a tissue engaging configuration, for example following deployment and expansion of the implant proximate a treatment site, and prior to anchoring the implant 400 to tissue. The frame 420 may have an overall axial height in the range of 15 to 20 millimeters (mm) in the tissue engaging configuration. This height or range of height will vary even further from this 15 to 20 mm range, depending on the size and pattern of the frame 420 and a length of the anchors 410. In some embodiments, the frame may have a height of approximately 17 millimeters.

Figure 5:
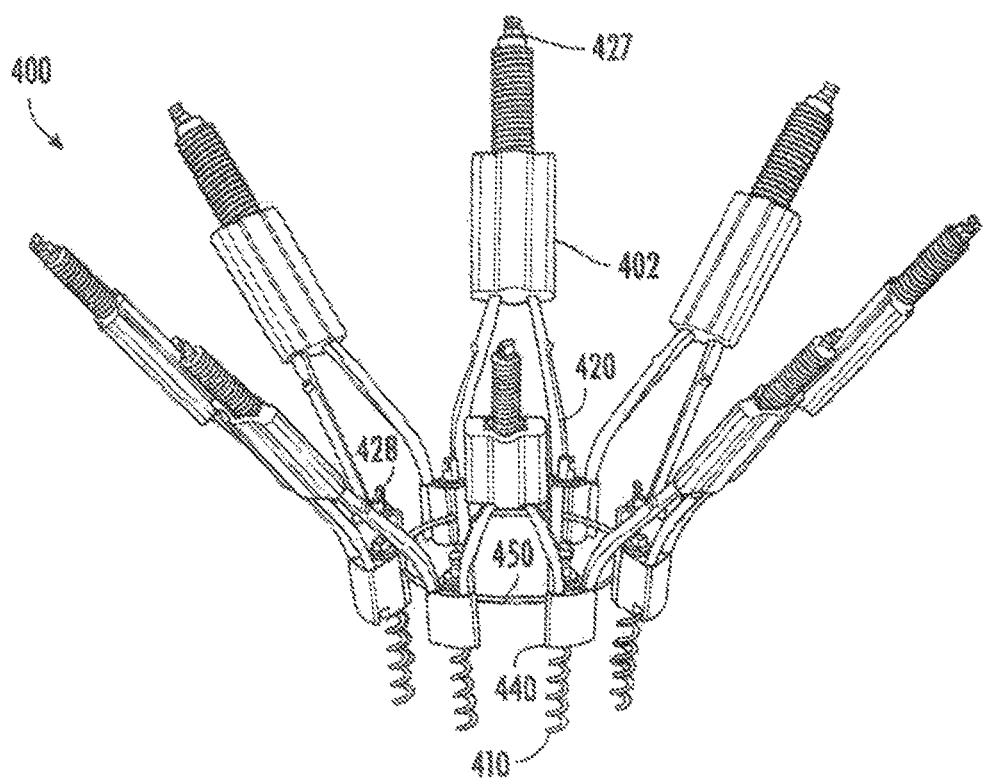
FIG. 5 is a diagram of an anchored and cinched implant in accordance with an embodiment of the present disclosure.

FIG. 5 depicts the implant 400 following anchoring of the implant 400 to tissue. The anchor 410 is shown in FIG. 5 to have been rotationally advanced through the anchor housing 440 such that a tissue piercing end of anchor 410 has rotationally advanced into the tissue. In FIG. 5, implant 400 is shown reconfigured to a contracted or cinched configuration. The cinched configuration of the implant 400 may correspond to an annulus remodeling diameter and/or an annulus remodeling height that differs from the tissue engaging configuration diameter and/or height. For example, the annulus remodeling height of the implant 400 may be greater than the tissue engaging height of the implant 400 in the tissue engaging configuration. The annulus remodeling diameter of the implant 400 may be less than the tissue engaging diameter of the implant 400 in the tissue engaging configuration. In various embodiments, due to the customizability provided by independently controllable actuators, the reduction in diameter may be asymmetrical. For example, before cinching, the implant 400 may be in a generally elliptical, oval or other shape, and after cinching the implant 400 may be in a general "D" shape or other shape (and with a relatively reduced circumference). Thus, the implant 400 may be in a variety of shapes before or after cinching, as well as during cinching. For instance, collars 402 may be advanced individually (e.g. not simultaneously). The implant 400 may thus have an irregular shape while being cinched. In some embodiments, even in the cinched state not all of the collars 402 are advanced, and/or are not all advanced the same amount, such that in the cinched state the angular displacements among different pairs of adjacent struts may not be the same. The implant 400 may thus be cinched in a custom manner depending on the particular patient's needs. In some embodiments, about half of the implant 400 may be cinched, for example to bring the anterior native leaflet closer to the posterior native leaflet, or vice versa. Thus, the "cinched" state of the implant 400 is not limited to only those particular shapes shown and described herein, but includes a multitude of possible shapes, sizes, etc. which may be chosen based on needs of the patient.

According to one aspect, the implant may include a retaining feature that retains the cinched shape of the implant following removal of the actuators. The retaining feature may be a physical component of the implant, such as cinch cord 450 extending through anchor housings 440, or alternatively may include a physical attribute of the frame that aids in retention as will be discussed in more detail later herein.

According to one aspect, a cinch cord 450 may include cinch wire, suture material or the like, and may be slideably disposed within cinch lumens of anchor housings 440, interconnecting the anchors in the cinched configuration of the implant 400 as shown in FIG. 5.

Figure 6A:
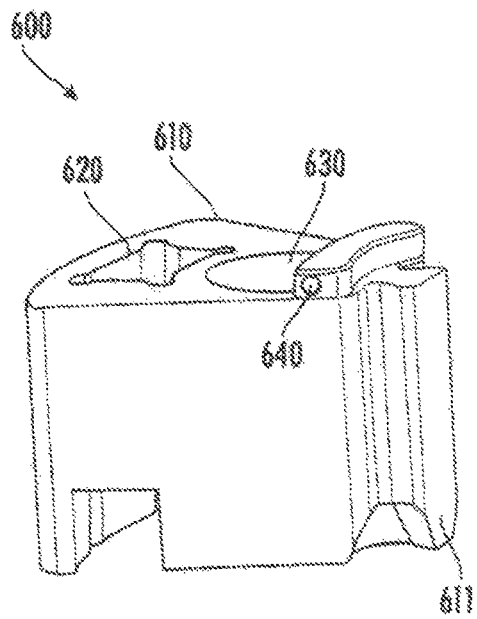
FIGS. 6A-6C illustrate embodiments of anchor housings configured in accordance with the present disclosure.
Figure 6B:
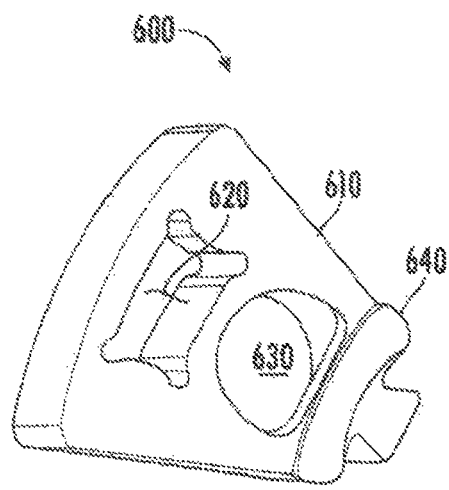
Figure 6C:
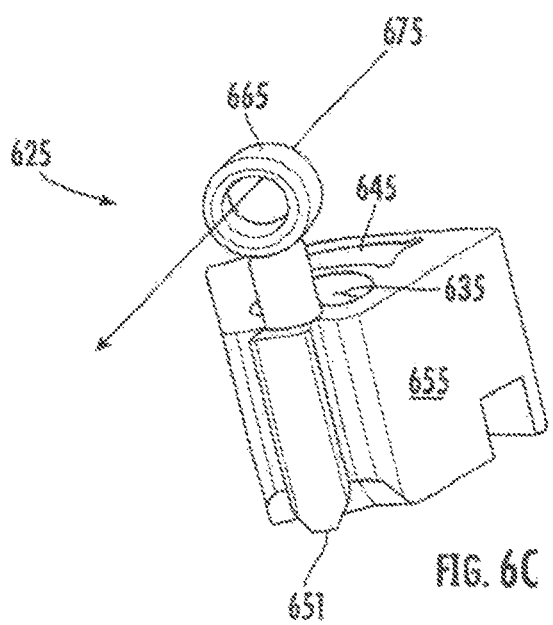

FIGS. 6A-6C illustrate exemplary embodiments of anchor housings 600, 625 which may be used to support the cinch cord 450 as described above. Anchor housing 600 is shown to include a body 610 having a plurality of lumens extending at least partially therethrough. For example, anchor housing 600 may include an anchor lumen 630 through which the anchor is advanced to attach the implant to tissue, and slot 620 for securing struts of the frame to the anchor housing. In some embodiments, the anchor housing may further include a flange 611. The flange 611 may be used in conjunction with a retainer (not shown), for retaining the anchor housings in a compressed configuration for deployment through a catheter.

The anchor housing 600 may further include a cinch lumen 640 that is configured to extend at least partially through the anchor housing body 610. For example, FIGS.

6A and 6B illustrate perspective views of an anchor housing body 610 through which a cinch cord may be advanced. The cinch lumens of the anchor housings, together with the cinch cords, in one embodiment may provide the retaining feature for retaining relative positions of anchors of a cinched implant. In one embodiment, the cinch lumen is positioned such that the cinch cord is positioned within or around an internal circumference of the frame. In other embodiments, the cinch lumen may be disposed about an outer circumference of the frame.

FIG. 6C illustrates an alternate embodiment of an anchor housing 625. Similar to anchor housing 600, anchor housing 625 is shown to include a body 655 having an anchor lumen 635, a slot 645 and a flange 651. Anchor housing 625 includes an eyelet 665 providing a cinch lumen 675. In one embodiment, the eyelet may advantageously be a swivel eyelet, which provides a greater degree of freedom and flexibility as a cinch cord is threaded between anchor housings. In FIG. 6C, the eyelet is shown disposed on a proximally oriented face of the anchor housing 625, though in other embodiments, the eyelet or other form of cinch lumen may be disposed on a distally oriented surface or another surface of the anchor housing 625.

In alternate embodiments, the cinch lumen may extend through the flange 651, in a configuration similar to that shown in FIG. 5, or alternatively through a different feature of the anchor housing. The present invention is not limited to any particular placement of a cinch lumen in or on the anchor housing.

According to one aspect, it is realized that the cinch cord 450 may advantageously be used to bind the implant in a compressed form for transluminal delivery to the treatment site. Such an arrangement may eliminate the need for flange 651, thereby minimizing the cross-sectional diameter of the pre-deployment implant.

Figure 7:
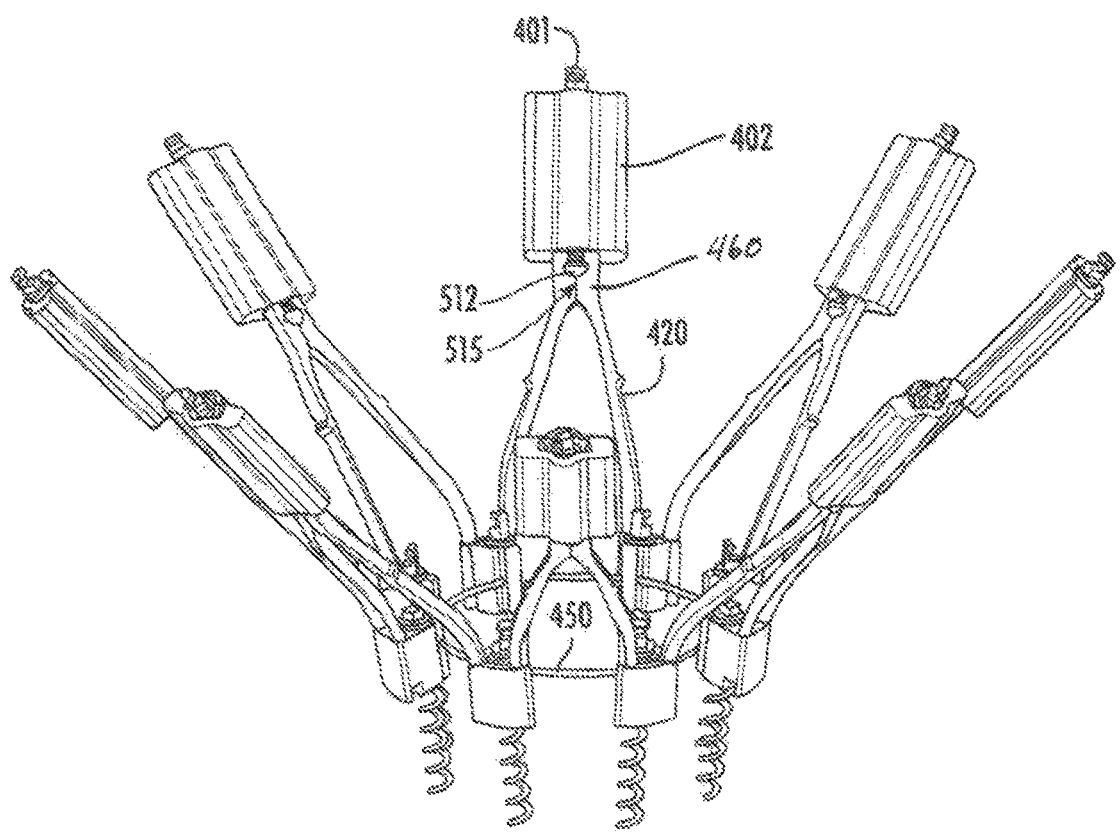
FIG. 7 is a diagram illustrating removal of actuators in accordance with an embodiment of the present disclosure.

As shown in FIG. 7, once the frame 420 is secured via the retaining mechanism (here cinch cord 450), the actuator collar 402 and shaft 401 may be released from the frame 420 and be withdrawn from the treatment site through the deployment catheter. As described above, releasing the actuators may include activating the shaft 401 to translate the collar 402 proximally at least until the shaft head 512 is exposed and releasable from the window 515 formed within the proximal apex 460 of the frame 420. In various embodiments, the actuators may be driven for release individually, simultaneously, or some combination thereof.

Figure 8A:
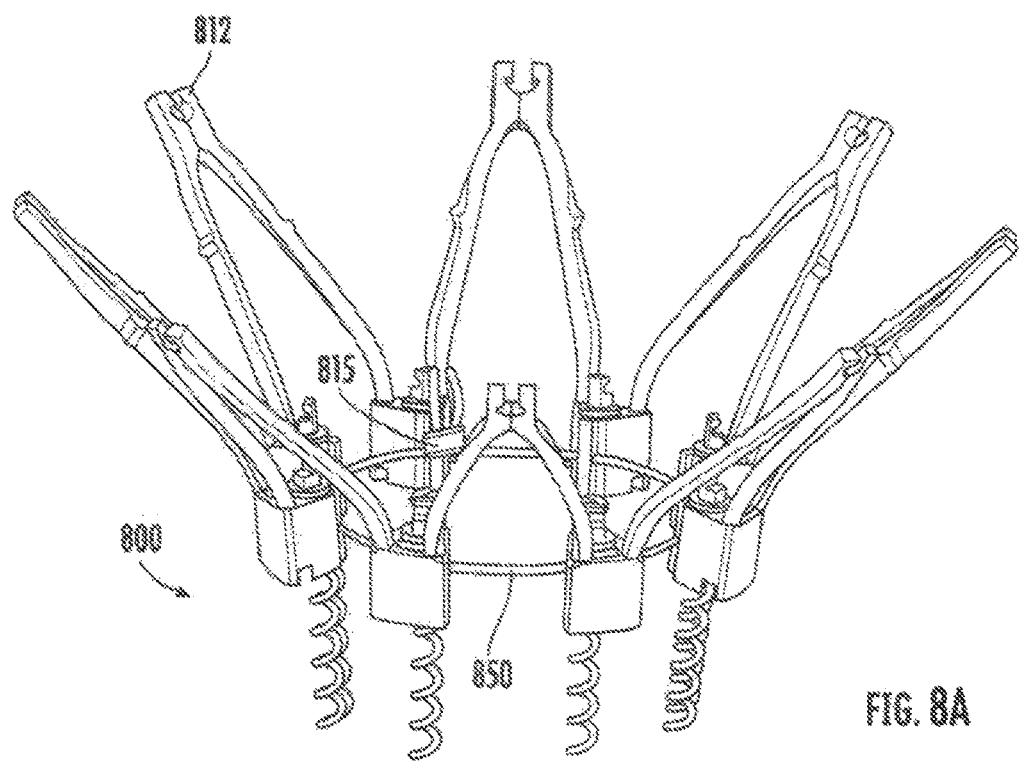
FIGS. 8A and 8B illustrate exemplary implants with removed actuators in accordance with one embodiment of the present disclosure.
Figure 8B:
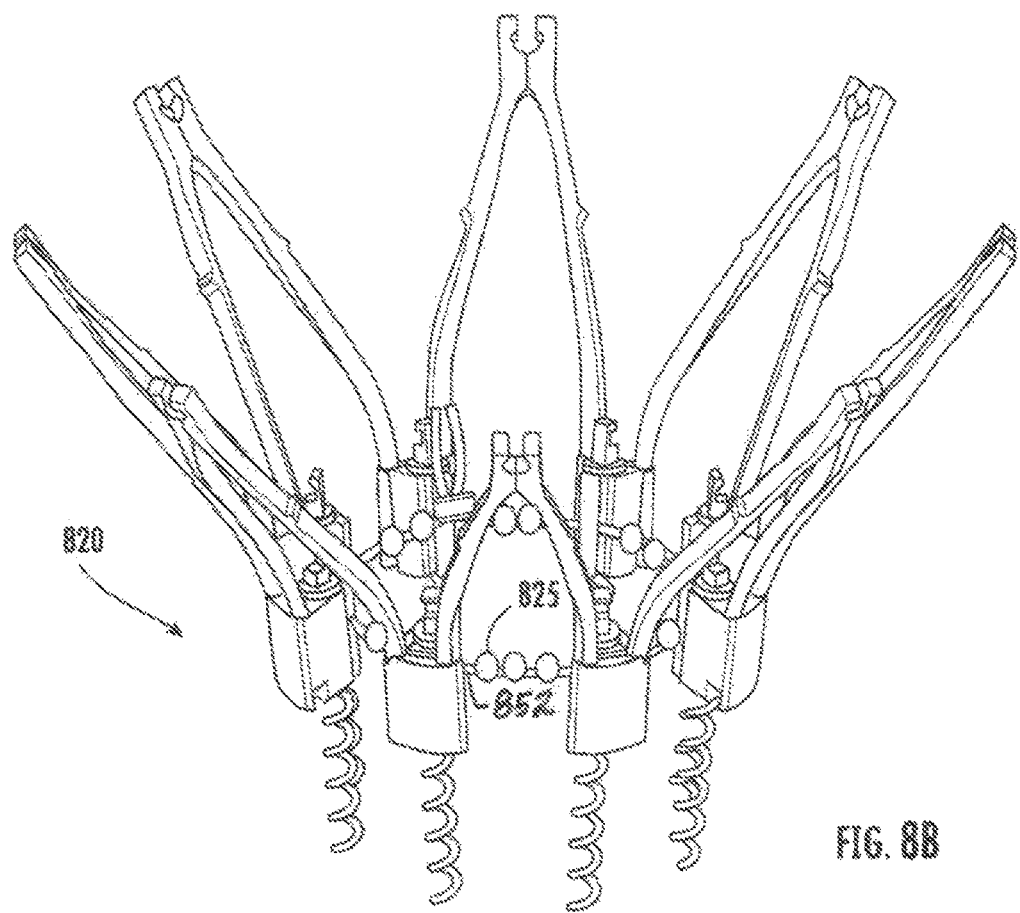

FIGS. 8A and 8B illustrate respective implants 800, 820 following release of actuators. As shown in FIG. 8A, the cinch chord 850 may be secured by tying or other method, such as a cinch clamp 815, a resistive weld band or other method. Removal of the actuators significantly reduces the height of the implant, reduces the number of components left within the atrium, removes ridged elements, such as screws, from the atrium and thus provides an implant with reduced fracture and other risks.

According to another aspect, because the frame need not support the actuator structure during chronic use, the frame may be formed of a lighter weight material. In some embodiments, a proximal apex 812 may be rounded to further reduce the impact of unintended contact between the implant and a heart features. While FIGS. 8A and 8B illustrate frames extending radially outward from the cinched diameter of the implant, in some embodiments the frame may be made from material that is biased radially towards a central axis of the frame to further minimize the potential of inadvertent contact.

FIG. 8B illustrates an implant 820 including a linked cinch cord 852. According to one aspect, as described later herein, in one embodiment the cinch cord may include a plurality of links, hooks or other features, such as link 825, which may be configured to advance in one direction through the cinch lumens, but resist travel in an opposite direction, much like a ratchet belt or other such type of restraint. Such embodiments may advantageously cinch the anchor collars together yet retain desired spacing between the anchor housings, further customizing implant reconstruction.

Accordingly, an embodiment of an implant including removable actuators has been shown and described to include mechanisms for expanding a compressed frame, actuating the frame to reshape the annulus, and attaching a retaining mechanism to the frame to retain the annular reshaping. In various embodiments, the removable actuators may be used in implants having different mechanisms of action for implant placement, implant actuation and actuator removal. Depending upon the mechanisms of action for a given implant, it is envisioned that modifications may be made to the collar to assist with deployment while enabling actuator removal.

Figure 9A:
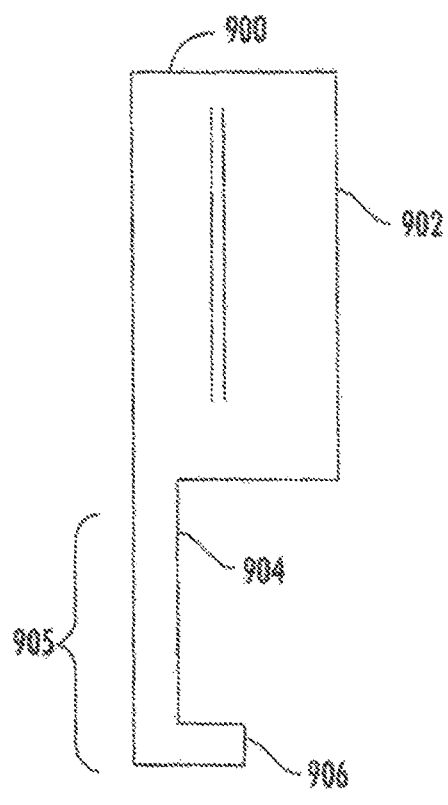
FIGS. 9A and 9B are perspective illustrations of one embodiment of a collar including a spreading mechanism in accordance with an embodiment of the present disclosure.
Figure 9B:
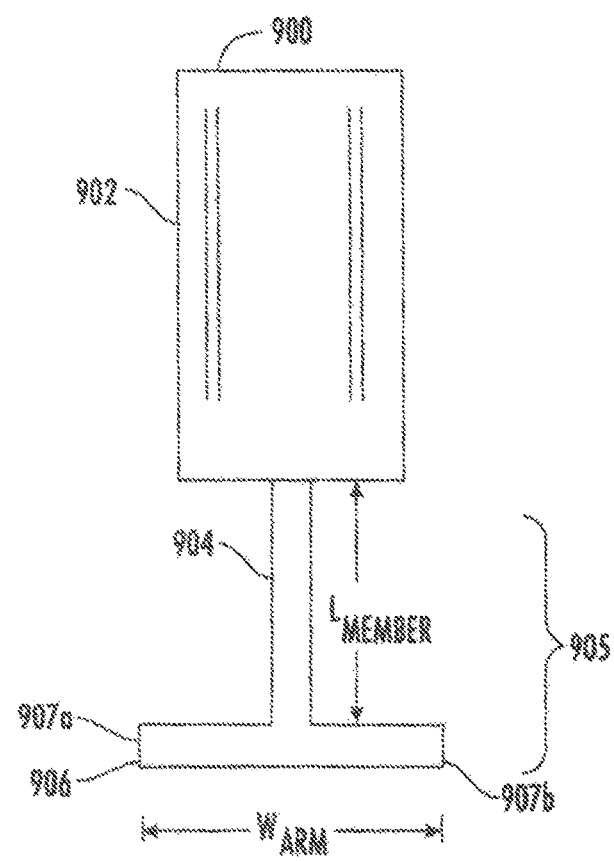

For example, FIGS. 9A and 9B are perspective views of one embodiment of a collar 900 that may be included as part of an actuator for use with a self-cinching implant, where a self-cinching implant may be an implant that is at least partially biased towards a compressed state, for example, a shape equal to or smaller than a target valve annulus. Collar 900 is shown to include a sleeve portion 902 which may be similar in design to the collar described with regard to FIGS. 3A-3D. Member 904 may be attached to or integral with the sleeve 902 and extend distally from the sleeve 902 along an axis parallel to a plane defined by struts of a frame. Extending from the member 904 is a spreader mechanism 905, including an arm 906, where the arm is configured to extend into the plane defined by coupled struts of the frame such that ends 907a, 907b engage the struts. A width $W_{Arm}$ of the arm 906 may be selected in accordance with a spacing between struts corresponding to an expanded state for a tissue engaging configuration. A length $L_{Member}$ of member 904 may be selected such that the arm 906 can expand the device to the tissue engaging configuration when the sleeve portion 902 is proximally actuated along the proximal apex. The length $L_{Member}$ may relate to the width $W_{Arm}$ of the arm 906. The width $W_{Arm}$ and length $L_{Member}$ of the member may be adjusted to optimize device spreading. Depending on the geometry of the proximal apex, the $W_{Arm}$ may be as low as 1-2 times the strut width, three times the strut width, or higher. The $L_{Member}$ may be between one quarter and one half the length of the strut.

Figure 10A:
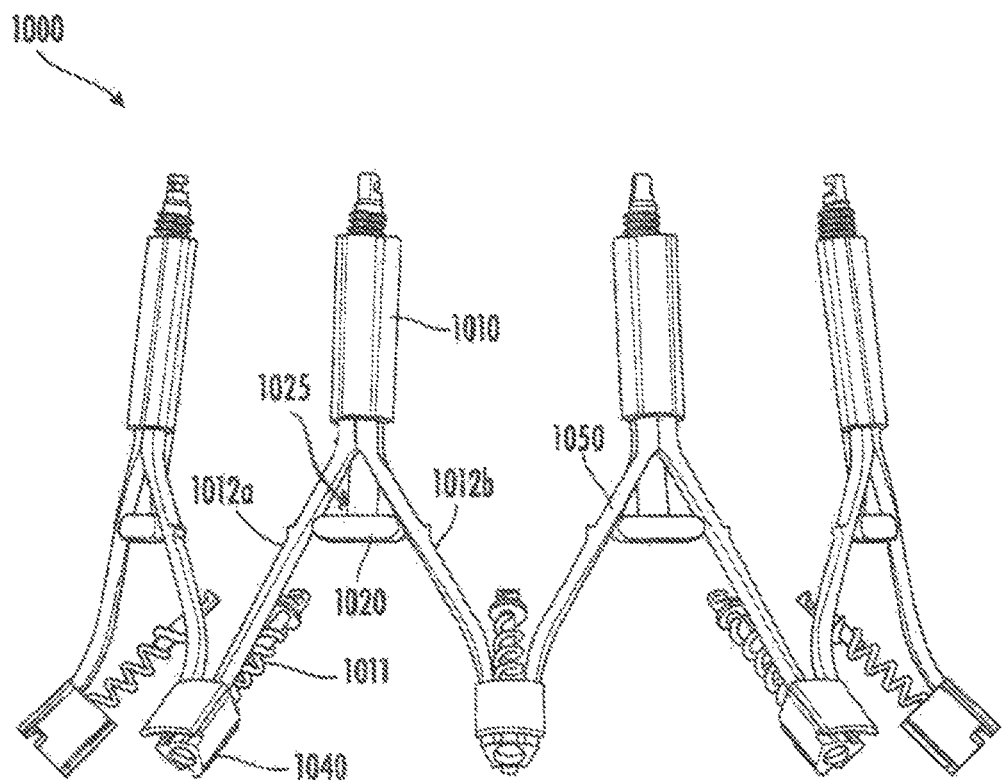
FIGS. 10A and 10B illustrate an exemplary implant including a spreader mechanism in a deployed and anchored configuration in accordance with an embodiment of the present disclosure.
Figure 10B:
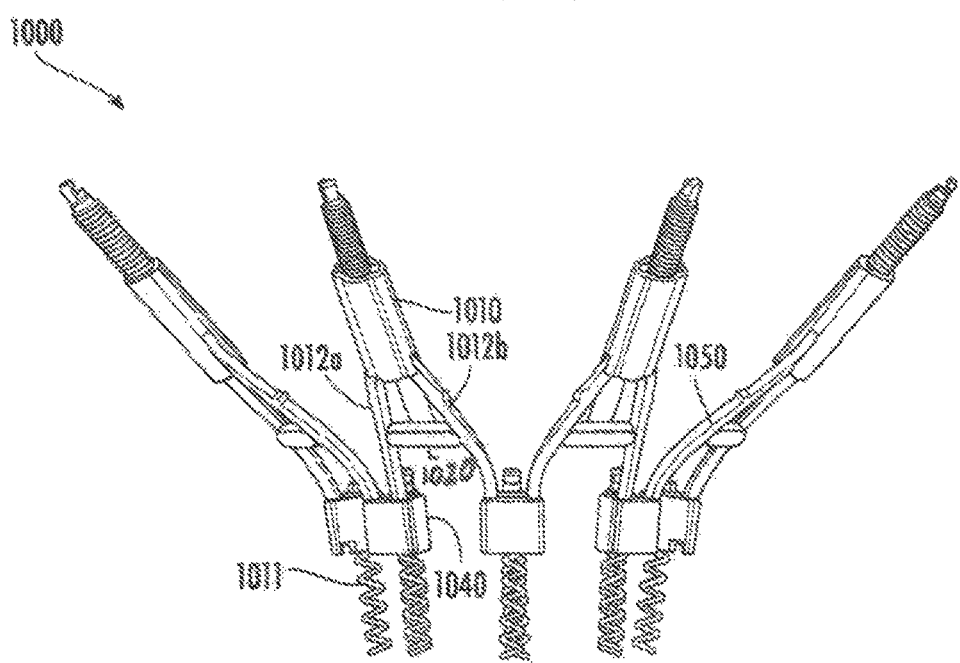

FIGS. 10A and 10B illustrate a portion of an implant 1000. Although only a relatively linear portion of the implant is shown, it is appreciated that the implant 1000 includes a generally tubular shaped implant for use in annular reshaping.

In one embodiment, the implant 1000 may include a frame 1050 formed of a heat set material that is biased towards a compressed configuration, for example biased towards a compressed configuration having a diameter related to the size of a valve annulus. According to one aspect, it is realized that the natural bias of the frame may be used as a retaining mechanism following placement, anchoring and actuation of the implant. In such embodiments, actuators 1010 including spreading mechanisms 1025 may be used to expand the frame 1050 to a tissue engaging configuration, for example by driving the actuator 1010 proximally along the struts 1012a, 1012b as shown in FIG. 10A. Proximal advancement of the actuator 1010 along the struts 1012a, 1012b causes the arm 1020 of the spreader mechanism 1025, which lies within the plane defined by struts 1012a, 1012b, to exert lateral force against the struts 1012a, 1012b, to expand the frame to a tissue engaging configuration. As shown in FIG. 10A, during positioning the distal ends of anchors 1011 may be disposed within the anchor housing 1040.

Once the frame 1050 is expanded to a tissue engaging configuration, anchors 1011 may be driven through anchor housings 1040 into the tissue as shown in FIG. 10B. In one embodiment, once the implant 1000 is secured by the anchors 1011 to the annulus, actuation may be performed to shape the annulus as described above. For example, the actuators 1010 may be independently driven over their respective struts to pull the anchors 1011 together to shape the annulus. As the actuator 1010 travels distally over the struts 1012a, 1012b, the arm 1020 similarly travels distally along a plane defined by the struts. As the arm 1020 travels distally along the plane defined by the struts, the force of the arm 1020 on the struts is reduced due to an increase in distal spacing between the struts. The reduction of the forces of the arms 1020 acting upon the struts 1012a, 1012b allows the struts 1012a, 1012b to return to various degrees of their biased configuration depending upon the distance traveled by the struts 1012a, 1012b. In an alternate embodiment, the implant 1000 may be positioned, the actuators 1010 distally advanced to shape the implant and then the anchors 1011 may be driven through anchor housing 1040 into the tissue to retain the actuated configuration.

Figure 11A:
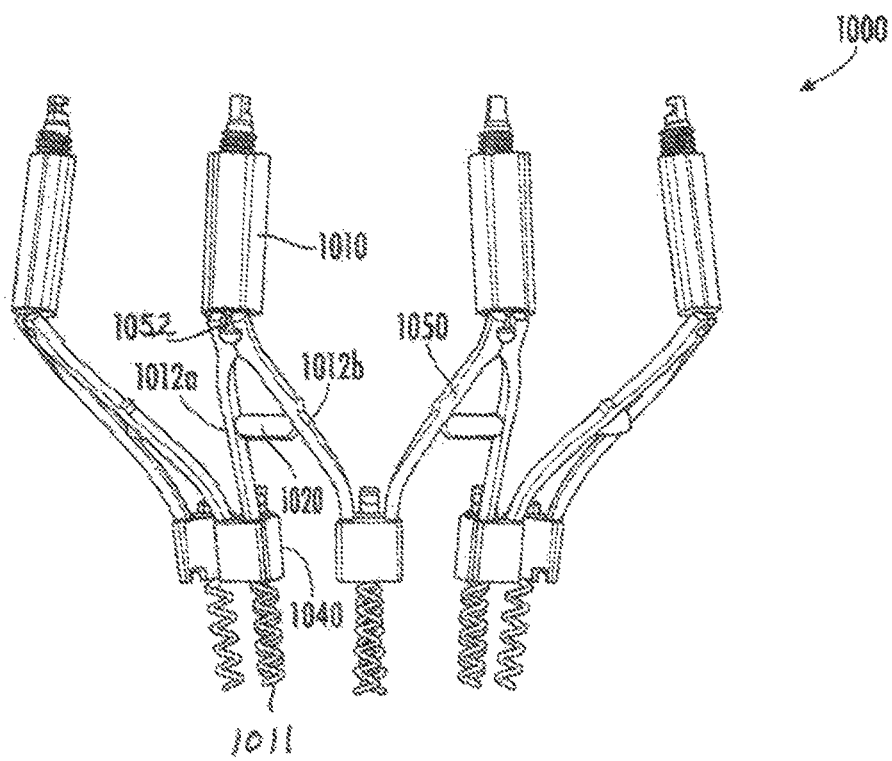
FIGS. 11A and 11B are diagrams illustrating removal of actuators including a spreader mechanism in accordance with an embodiment of the present disclosure.
Figure 11B:
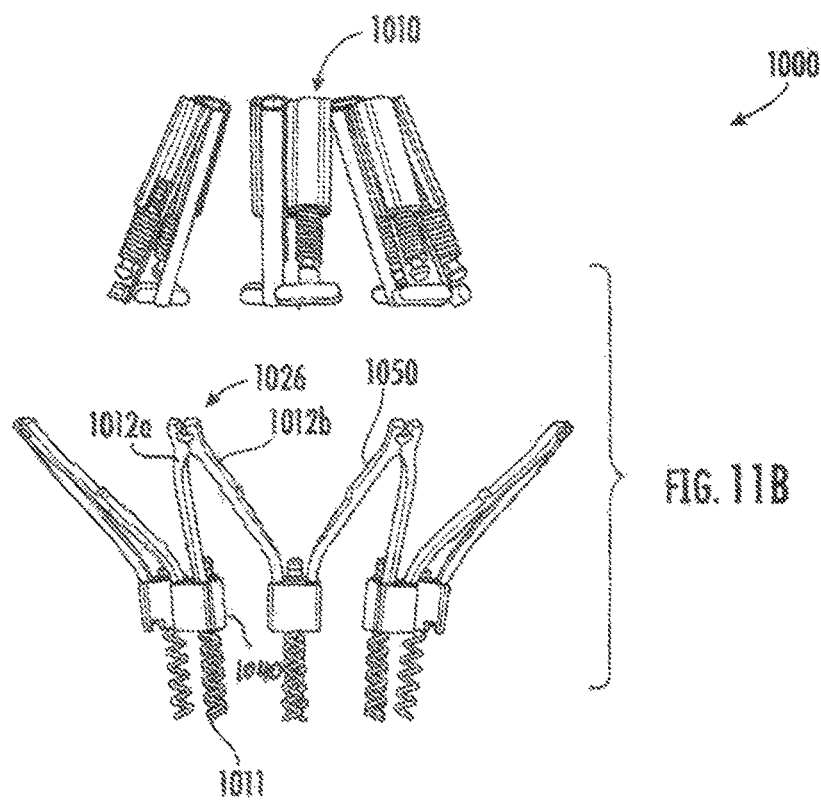

FIGS. 11A and 11B illustrate the release of the actuators 1010 following anchoring by translation of anchors 1011 through anchor housing 1040. Actuator 1010 may be proximally advanced over the struts 1012a, 1012b until the shaft head 1052 is exposed and releasable from the proximal apices of frame 1050 as shown in FIG. 11A. Release of the shaft head 1052 from frame 1050 also removes arm 1020 from between struts 1012a, 1012b. Release of the actuator 1010 from the frame 1050 allows the frame 1050 to return to a biased, cinched, configuration. As shown in FIG. 11B, the released actuators 1010 may then be withdrawn through the deployment catheter from the treatment site. As a result, only the frame 1050, anchors 1011 and anchor housings 1040 remain. As discussed with regard to FIGS. 8A and 8B, in one embodiment the proximal ends 1026 of struts 1012a, 1012b of the frame 1050 may be curved or otherwise blunted to minimize trauma caused by inadvertent contact of the implant with heart features. In various embodiments, the frame 1050 may be heat set to bias the struts 1012a, 1012b radially inwards towards a central axis of the frame 1050 when released by the actuators 1010 to further limit the potential for inadvertent contact.

Accordingly, various embodiments of annular valve implants providing customizable valve shaping with removable actuators has been shown and described. Such implants may be part of a transluminally delivered valve annulus reshaping system 1200 such as that shown in FIG. 12 which is shown to include a deployment catheter 1210 comprising a distal sheath 1240 having a distal tip 1220 coupled to an extendable guidewire 1225. During implant deployment, the deployment catheter 1210 may be advanced transluminally using the guidewire 1225 to a treatment site, for example in an atrium 1265. Guide wire 1225 may measure, for example, between 0.010 inches and 0.038 inches in diameter. Deployment catheter 1210 may measure about twenty to thirty centimeters in length for accessing the mitral valve through the apex of the heart. Deployment catheter 1210 may access the heart through the vasculature of the leg, for example the femoral vein or the iliac vein for transluminal deployment to a cardiac annulus.

Figure 12:
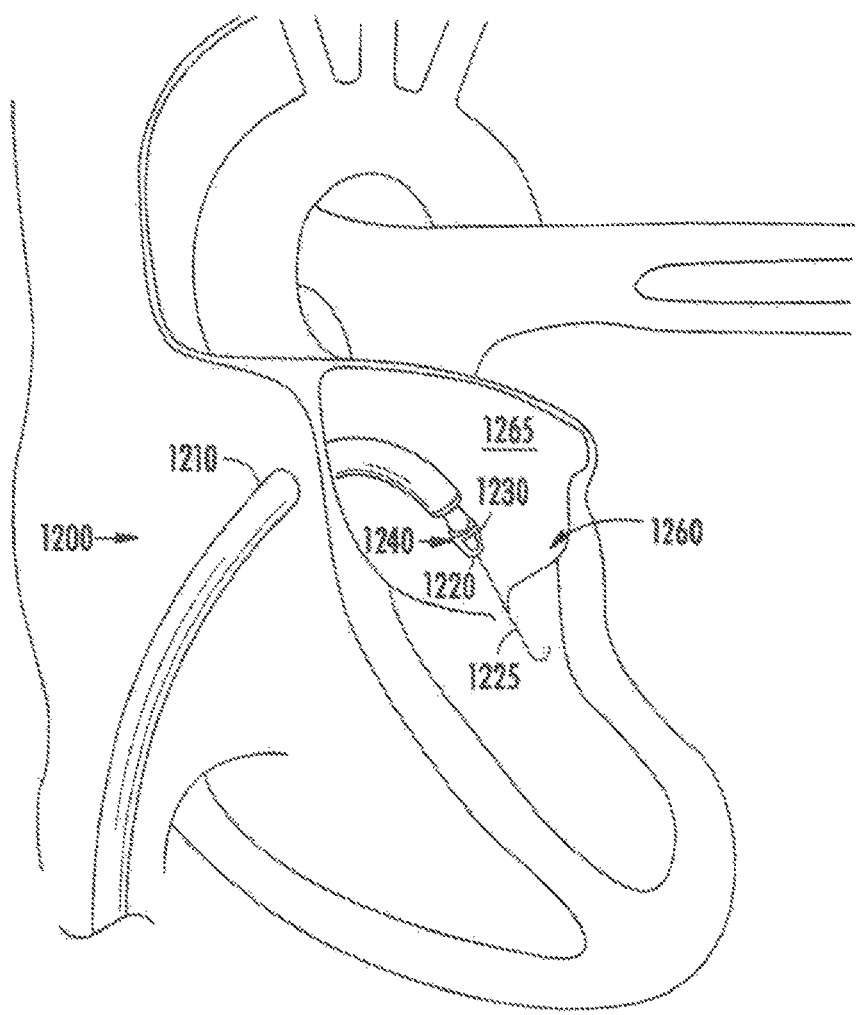
FIG. 12 illustrates introduction of an exemplary implant as disclosed as part of an exemplary implant delivery and actuator removal method of the present disclosure.

An implant 1230 including removable actuators such as those disclosed herein may be disposed within the distal sheath 1240 of the deployment catheter during deployment. In FIG. 12 the distal tip 1220 of the deployment catheter 1210 is shown maneuvered into the left atrium 1265 to a treatment position proximate to a mitral valve annulus 1260. Following deployment to the treatment site, the implant may be released from the deployment catheter, expanded to a tissue engaging configuration, cinched to a valve reshaping configuration, and anchored proximate the mitral valve. As described herein, thereafter the actuators may be released from the frame and withdrawn through the deployment catheter 1210.

Figure 13:
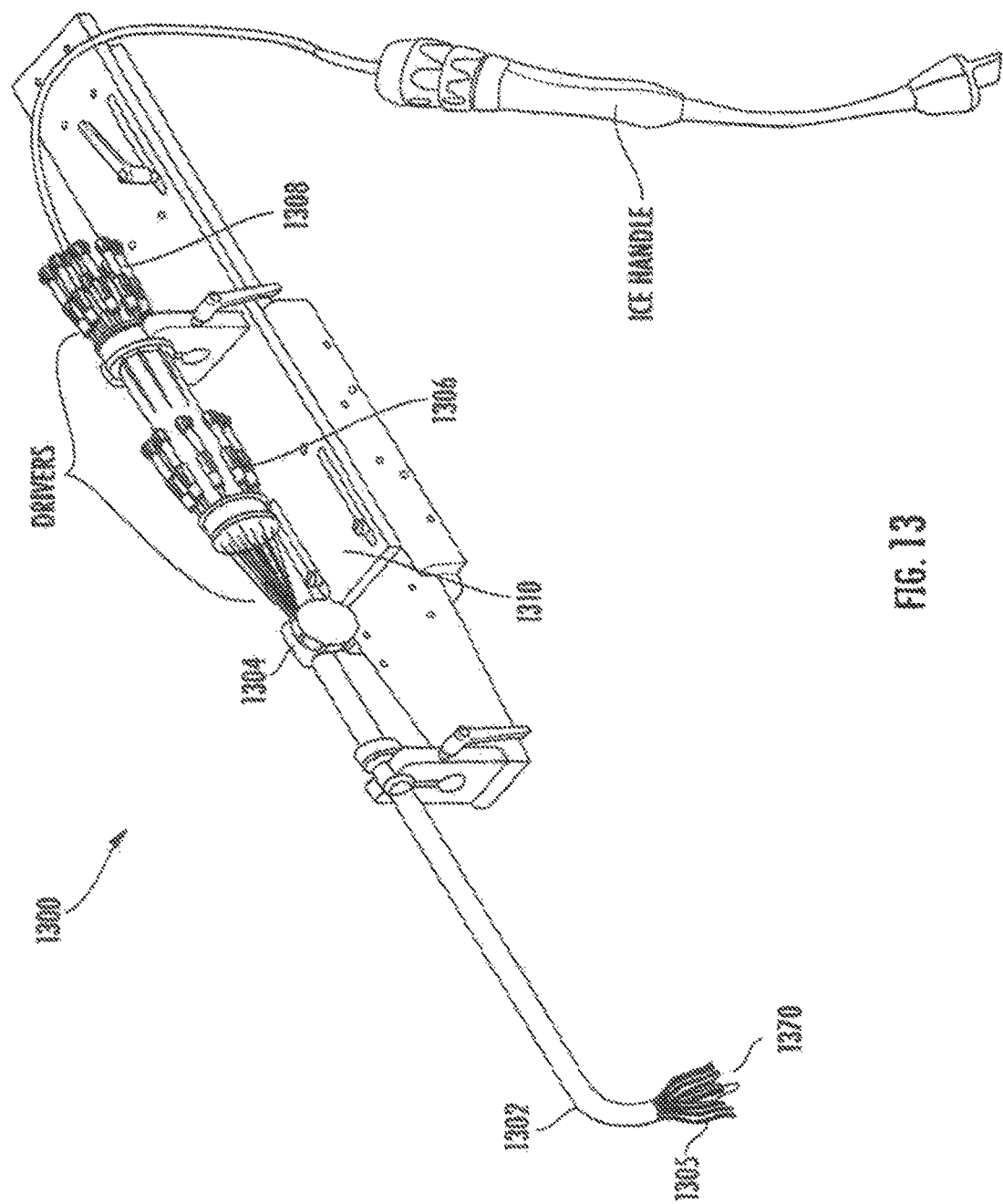
FIG. 13 illustrates an exemplary deployment device for use with embodiments of the implant in accordance with the present disclosure.

FIG. 13 illustrates an exemplary deployment system 1300 that may be used to deploy an implant 1305 for annular reshaping as described herein. The deployment system 1300 includes a steerable sheath 1302, a sheath steering knob 1304, anchor knobs 1306, cinch knobs 1308, and an Intra-Cardiac Echocardiography (ICE) probe 1370, all supported and secured to a base 1310. The cinch knobs 1308 and anchor knobs 1306 may be spring loaded to maintain tension. Rotation of the anchor knobs 1306 may rotationally advance anchors of the implant into annular tissue. Cinch knobs 1308 may be manipulated by an operator to compress an expandable frame, coupled to the anchors, to reduce a valve annulus, as well as to remove the actuators from the frame to provide the low profile implant. It should be understood that the present invention is not limited by the mechanisms used to drive the actuators described herein, and that other implementations may be substituted herein without affecting the scope of this disclosure.

Various embodiments of an implant delivery system having removable collar-based actuators to enable a customizable, low profile valve reconstruction solution have thus been described. It is appreciated that the principles disclosed herein may be applied to other implant delivery systems that use different actuation mechanisms by those of skill in the art.

Figure 14:
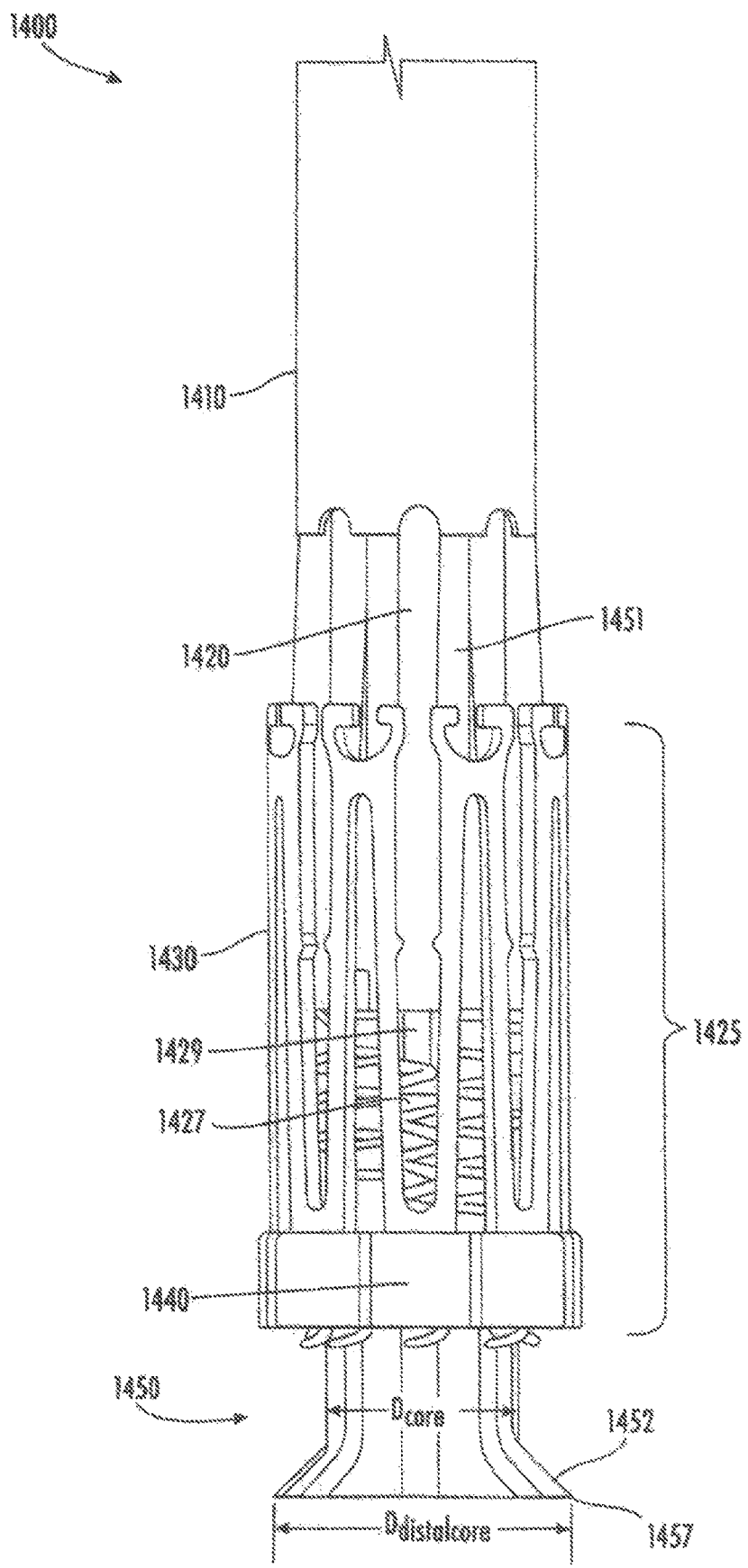
FIG. 14 illustrates an exemplary embodiment of an implant delivery system comprising removable actuators as disclosed herein.

For example, FIG. 14 illustrates an implant deployment system 1400. Such implant deployment system 1400 may be carried within the distal sheath 1240 (FIG. 12) of a deployment catheter (1210, FIG. 12) and delivered to a valve annulus as described with regard to FIG. 12. The implant deployment system 1400 is shown including an implant 1425 comprising a resilient frame 1430 having anchor housings such as anchor housing 1440 disposed upon one or more distal apex of the frame 1430. Each anchor housing 1440 may be configured to translatably support an anchor 1427.

The implant deployment system 1400 also includes a sleeve 1410 which may be formed, for example, from an extruded polymer such as PEBAX provided by ARKEMA corporation of Colombes France. Alternatively, nylon, polyurethane, polyester, silicone or other similar materials may be used to provide thin walls that may be extruded and layered over braided wires or coils for tensile and hoop strength, although the disclosed system is not limited to any particular material composition for the introducer catheter.

A plurality of flexible tubes, such as tube 1420 may be affixed or otherwise coupled to the sleeve 1410 at their proximal ends, such that the tubes 1420 are cantilevered relative to the sleeve 1410. A drive shaft 1429 may extend through each of the flexible tubes 1420 to engage and drive the coupled anchor 1427 through the anchor housing 1440 into annular tissue.

In one embodiment, a core 1450 may be disposed within a central lumen of the sleeve 1410. In some embodiments, the core may have a lumen extending therethrough, for example, for translational support of working catheters and/or visualization devices such as the ICE probe 1370 (FIG. 13). According to one aspect, the core 1450 may include a core shaft 1451 extending to one or more flanges 1452 at its distal end, wherein one or more flanges 1452 extends radially to a distal edge 1457 such that an external diameter $D_{distalcore}$ is greater than an external diameter of the core shaft $D_{core}$. In one embodiment, the flange 1452 may taper proximally from a diameter of $D_{distalcore}$ to $D_{core}$ to facilitate translation of the core 1450 proximally past anchor housings 1440. In various embodiments, the core 1450 may be unitary to form a sleeve disposed within the sleeve 1410. In other embodiments, as described later herein, the core 1450 may include discrete, independently controllable arms configured to customize shaping of the frame 1430.

According to one aspect, each tube 1420 includes a flexible portion proximate to its proximal connection with the sleeve. The flexible portion enables the tube 1420 to flare angularly away from a central longitudinal axis of the sleeve 1410 when pressure is applied to the tube by the flange 1452 of the core 1450. During proximal translation of the core 1450, the distal edge 1457 of the flange 1452 pushes against the tube 1420 to deflect the tube radially outward from a central axis of the sleeve 1410. Because the tube 1420 is joined to the anchor housing 1440 via the driver 1429 and anchor 1427, and because the anchor housing 1440 is coupled to frame 1430, proximal translation of the core 1450 also acts to expand the frame 1430. In various embodiments, the core 1450 and flange 1452 thus include axially translatable adjustment components configured to control expansion and/or contraction of an implant frame 1430.

Thus, according to one aspect, the core 1450 is translationally disposed within the sleeve 1410. Deploying the system 1400 to the mitral valve may include the steps of advancing the distal end of a deployment catheter transluminally into the heart chamber and either withdrawing the introducer sheath or advancing the system 1400 past the distal end of the introducer sheath to position the implant within the heart chamber. The core 1450 may be positioned as shown in FIG. 14, such that the core 1450 and the flange 1452 extend beyond the anchor housings 1440, and the frame 1430 is held in a compressed state to minimize the diameter of the system 1400 during transluminal advancement of the implant 1425. In the compressed state, the frame 1430 may lie flush against the core 1450 as shown in FIG. 14. In alternate embodiments, the frame 1430 may be biased towards a semi-compressed state, for example, a state wherein a biased diameter of the frame 1430 corresponds to a shape and/or diameter of a healthy valve annulus. In such embodiments, the frame 1430 may be held flush against the core during delivery by pressure of the deployment catheter (1210 FIG. 12) on the frame 1430, and removal of the deployment catheter 1210 from the frame 1430 for deployment and/or body heat acting on the frame following insertion may cause the frame 1430 to expand to the semi-compressed state.

Figure 15A:
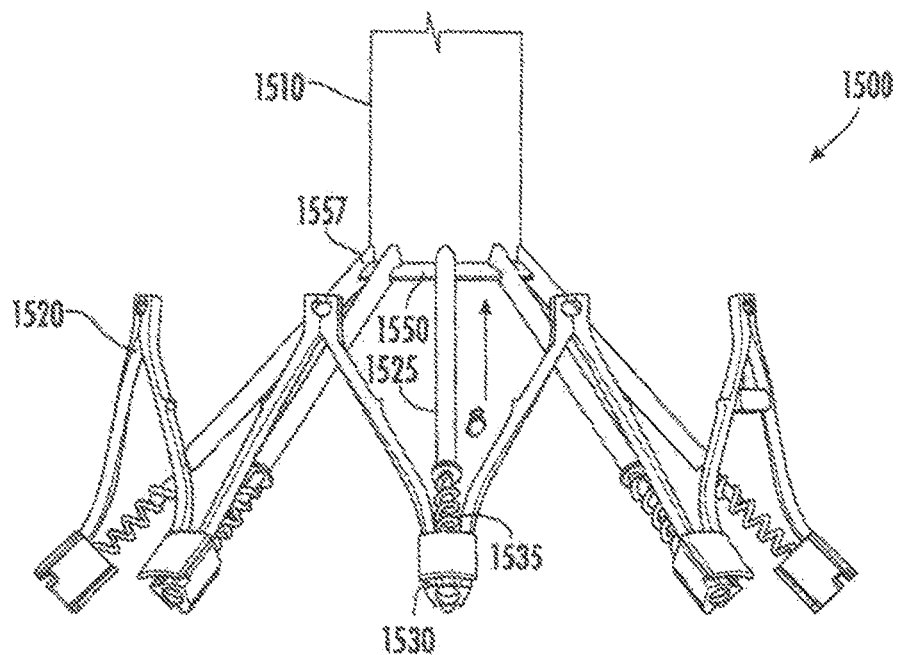
FIGS. 15A and 15B illustrate one embodiment of an implant delivery system as disclosed herein in an expanded configuration.

Referring now to FIG. 15A, following delivery of the implant 1500 to the heart chamber, the frame 1520 may be expanded to position the anchors, such as anchor 1535, in a tissue engaging configuration. According to one embodiment, expansion of the frame is controlled by translating the core 1550 proximally within the sleeve 1510 as indicated by arrow B. Proximal advancement of the core 1550 within the sleeve causes the flange 1557 of the core 1550 to apply force to the tubes, such as tube 1525, deflecting the tube 1525 angularly away from the longitudinal axis defined by the sleeve 1510. The tube 1525 in turn urges anchor housing 1530 radially outward, expanding frame 1520.

Figure 15B:
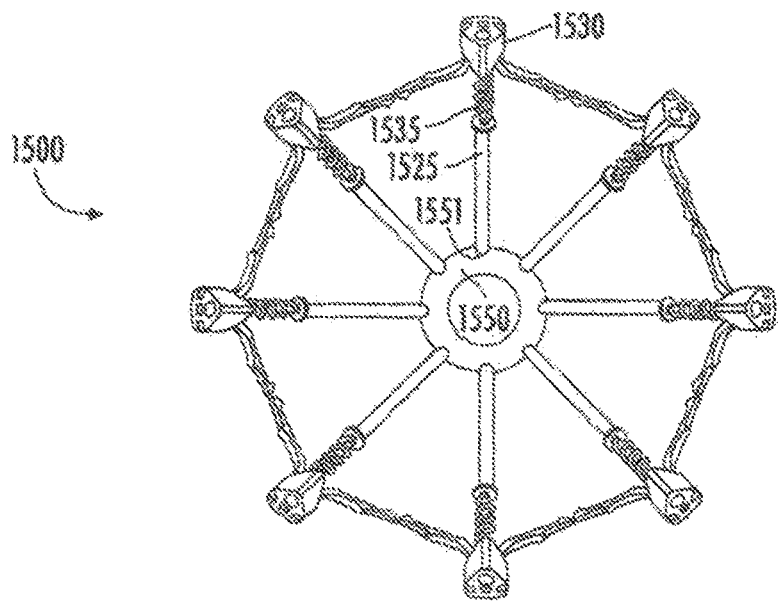

FIG. 15B is a proximally facing perspective view of the expanded implant 1500, for example via a perspective identified by arrow B in FIG. 15A. In the illustrated embodiment, a proximal end of the tube 1525 is slideably disposed within a detent 1551 provided on the flange of the core 1550. The implant 1500 is shown in an expanded state for tissue engagement. Once so configured, drive shafts within the flare tubes 1525 may be activated to drive anchors 1535 through anchor housing 1530 for tissue engagement. In one embodiment, the drive shafts may be torque shafts which rotate to drive the anchors 1535 through the anchor housings 1530 to engage tissue. Accordingly, in various embodiments the drive shafts may axially translate distally into and/or through the anchor housings to further fine tune expansion and/or contraction of an implant frame.

Figure 16:
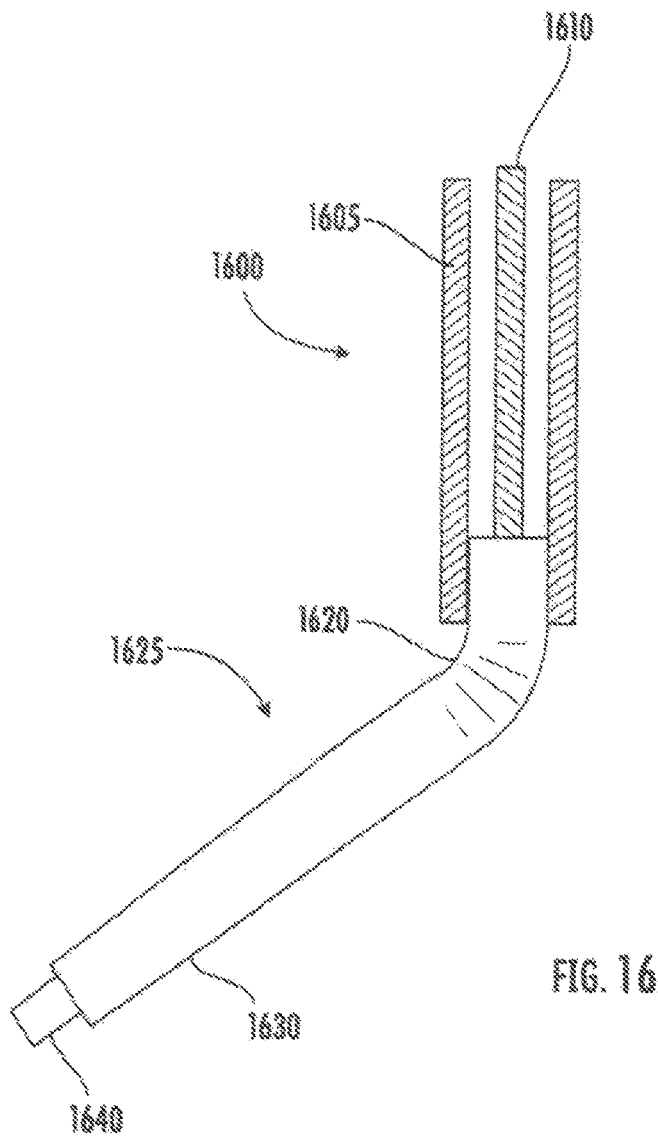
FIG. 16 illustrates an exemplary embodiment of a flare tube configuration as disclosed herein.

FIG. 16 illustrates one embodiment of a portion of an actuator 1600 that may be used to control expansion, anchoring and cinching of an implant frame as disclosed herein. The actuator 1600 is shown to include a sleeve 1605 (shown in cross-section) having a tube 1625 coupled or affixed near a distal end of the sleeve 1605. According to one embodiment, the tube 1625 may not be fully affixed to the sleeve 1605, but rather may be relieved from affixation along at least a portion of the outer contact surface of the tube to form a rotational joint at a flexible portion 1620. The rotational joint formed by flexible portion 1620 enables the tube 1625 to flare away from an axis defined by the sleeve 1605 as the implant is expanded. Accordingly, a tube such as tube 1625 having a flexible portion enabling the tube to form a rotational joint may be referred to herein as a 'flare tube'.

The flexible portion 1620 of flare tube 1625 may be disposed near a proximal end of the tube outside of the sleeve 1605, and a relatively rigid portion 1630 of the flare tube may extend from the flexible portion 1620 through the distal end of the tube 1625. The flexible portion may be formed by modifying the tube, for example by cutting way portions of the tube to increase flexibility. Alternatively, the tube may include a resilient sheath (such as a braided catheter or the like) which includes a relatively flexible polymer coating at the flexible portion 1620 and a relatively stiffer polymer coating along portion 1630. In some embodiments, the flare tube may be constructed from coated braid with varied braid, or composite with varying weave. In addition, some designs may find it helpful to decrease stiffness in only one direction (radially) while remaining stiff otherwise (circumferentially). According to one embodiment, the flare tube may increase in stiffness and/or decrease in elasticity as the flare tube extends distally. Providing increased stiffness as the tube extends distally allows the flare tube to more easily deform/bend to fine tune anchor spacing while providing sufficient distal stiffness to drive the anchor into the tissue.

According to one embodiment, a drive shaft 1610 may extend through the sleeve 1605 and through the distal end of tube 1625 to engage an anchor (not shown). In one embodiment, the drive shaft 1610 is a torque shaft including a coupler 1640 for engaging a proximal end of an anchor.

According to one aspect, the drive shaft 1610 may be configured to translate axially within the sleeve 1605 and tube 1630. An actuator such as actuator 1600 may be provided for each anchor, and the independent, axial movement of the drive shaft 1610 within the sleeve 1605 and tube 1625 may be used to push/pull or otherwise independently adjust the length between the various anchor heads and their associated flare tubes to fine tune configuration adjustments to the implant provided by the proximal translation of the core. Such an arrangement enables the implant to be configured in accordance with the particular needs of the patient and/or diseased state of the valve.

FIGS. 17A-17C illustrate various views of an alternate embodiment of a core 1710 that may be used to flare out the tubes as described with regard to FIG. 15A. In FIG. 17A, core 1710 is shown to include a plurality of arms, such as arms 1715a, 1715b and 1715c, each arm including or supporting a flange 1720a, 1720b, 1720c. Each arm may be disposed within the sleeve (not shown) and configured to extend from a proximal end of the sleeve through the distal end of the frame as shown in FIG. 14. Each arm is advantageously configured for independent axial translation. For example, the handle as shown in FIG. 13 may be adapted to include rotational knobs that advance and retract stiff wires or rods attached to the arms which may extend proximally to the handle to enable user manipulation. Each flange 1720a, 1720b, 1720c is shown to include a detent 1721a, 1721b, 1721c configured to support a flare tube. In one embodiment, each flange 1720a, 1720b, 1720c tapers proximally from a distal edge diameter to approximately the outer diameter of the core to facilitate translation of the anchor housings proximally past the flanges 1720a, 1720b and 1720c as the core is withdrawn proximally into the sleeve during frame expansion.

FIG. 17B is a proximally facing perspective of the distal end of a core 1710 comprising eight independently translatable arms, coupled to eight flanges 1720a-1720h. Although eight arms are shown, it should be understood that particular number of arms used is a matter of design, and equivalent embodiments may include, for example, as few as one or two or as many as eight, ten or a maximum number in accordance with available space in the deployment catheter. The detents 1721a-1721h may be complementary in profile to a tube profile, for example curved to provide a rail type support for the circular flare tube as the core is translated within the sleeve. The ability to independently translate each arm 1720a-1720c of the core 1710 further enhances the ability of the actuation system to customize the configuration of the implant by enabling the extent of deflection to be customized for each tube.

FIG. 17C illustrates the core 1710 with each arm 1715a-1715d translated to different proximal extents, resulting in different degrees of angular deflection for each tube supported by the flanges 1720a, 1720b, 1720c and 1720d. For example, arm 1715b, coupled to flange 1720b extends further distally than arm 1715d, coupled to flange 1720d. As a result, the flare tube supported by flange 1720b will have a lower angular expansion than the flare tube supported by flange 1720d. As a result, the anchor driven by a driver extending through a flare tube supported by flange 1720b may be positioned closer to a central axis of the core 1710, and a flare tube supported by flange 1720d may be positioned relatively farther from a central axis of the core 1710. With such an arrangement, asymmetric configuration of the implant may be achieved through both independent actuation using the core, and independent control of the drive shafts to push and/or pull the anchors to shape the implant prior to affixation. Providing two mechanisms for implant configuration, for example using core flange positioning for initial asymmetric shaping and the drive shafts to fine tune positioning, improves the ability to customize the implant for its particular purpose.

Figure 18A:
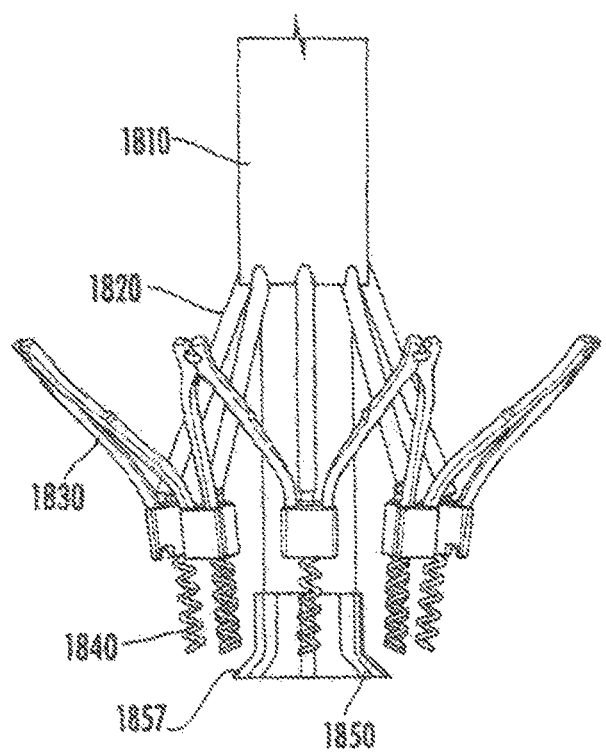
FIGS. 18A and 18B illustrate an embodiment of an implant delivery system as disclosed herein.

FIG. 18A illustrates an embodiment of the frame 1830 in an anchored configuration, with anchors 1840 configured to embed in tissue, for example by rotating or otherwise manipulating the drive shafts within the flare tubes 1820. Once the anchors 1840 are embedded in tissue, the core may also be advanced distally from sleeve 1810, releasing the force of the flanges 1857 on the flare tubes 1820.

According to one embodiment, the frame 1830 may be a 'self-cinching' frame (e.g. a frame formed of a resilient, shape memory material such as Nitinol or the like) that is biased towards the compressed configuration. As the core is advanced distally, the pressure exerted on the flare tubes 1820 and their associated anchor 1840 is relieved, and the frame 1830 returns to its biased configuration, drawing the affixed anchors together to reduce the annulus.

Figure 18B:
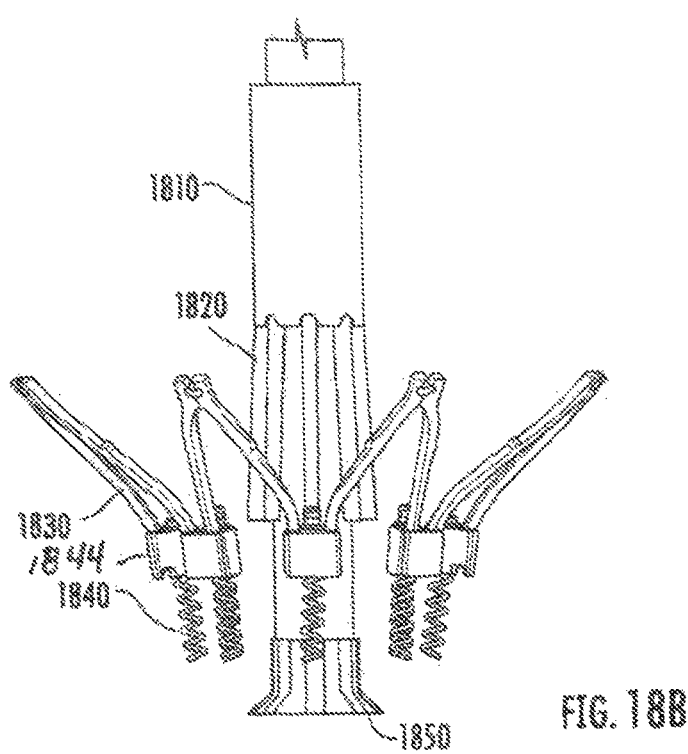

Following anchoring and cinching, the actuator system including the tubes 1820 and sleeve 1810 may be removed from the treatment site. As shown in FIG. 18B, in one embodiment the drive shafts are released from the anchor heads and withdrawn through the tubes 1820 and proximally through sleeve 1810. The flexible portion of the flare tubes allow the tubes to realign with the longitudinal axis of the sleeve for ease of removal. In some embodiments, the tubes 1820 may be formed at least in part from a shape memory based material that urges the tubes to a position flush against the core to facilitate removal. In some embodiments, following release of the drive shaft from the anchor heads, the sleeve 1810, core 1850 and tubes 1820 may be withdrawn back through the deployment catheter from removal from the heart cavity, leaving only frame 1830, anchor housings 1844 and anchors 1840.

FIG. 19A illustrates an alternate embodiment of an implant delivery system that includes a sleeve 1910 having flare tubes 1930 disposed therein, a core 1940 comprised of independently translatable arms, a frame 1950, at least one anchor housing 1960 and at least one anchor 1970. According to one aspect, an inflation device, such as a balloon 1945, may be inserted through a lumen 1920 of the core 1940, expanding outwardly from the core to engage the flare tubes 1930. Similar to the method disclosed above, the core may include independent arms that are proximally translated to adjust the angular deflection of flare tubes 1930 to shape the frame 1950. According to one aspect, manipulation of the flare tubes 1930 and/or arms of the core is controlled via a balloon 1945, wherein the balloon applies forces to the core and/or the flare tubes when expanded. Applying pressure to the arms of the core 1940 and/or flare tubes 1930 changes the angular deflection of flare tubes to move anchor housings 1960 to thereby reshape the frame 1950.

Figure 19B:
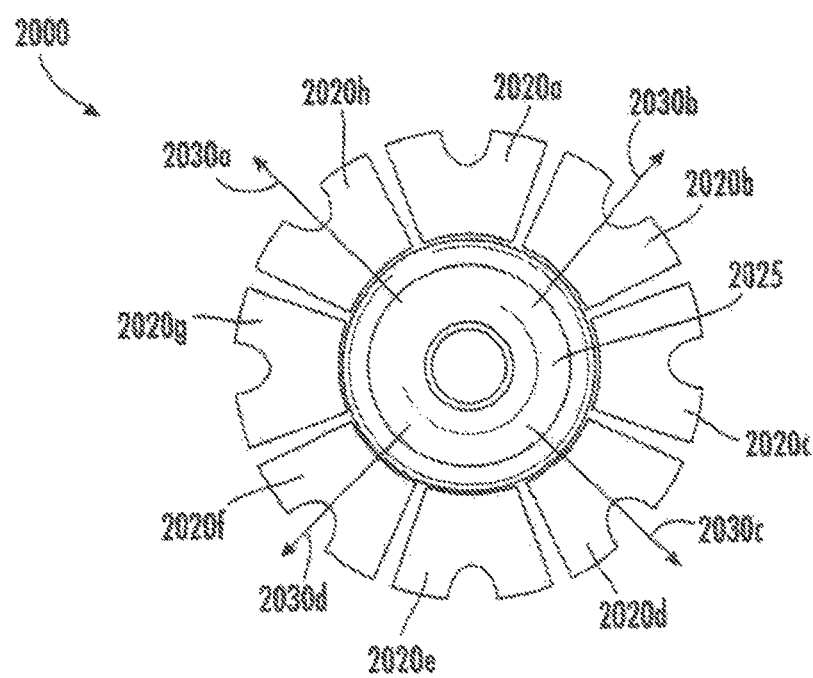

Accordingly, the balloon 1945 may be used in coordination with the arms of the core 1940 and the flare tubes 1930 to shape the frame. For example, in some embodiments, the balloon may be asymmetrically shaped, for example saddle shaped to match the shape of an annulus. In some embodiments, the balloon may be used without a core. The balloon, when inflated, may expand beyond the edge of the core 1940. The pressure of the balloon 1945 on the flare tubes 1930 may assist in the expansion of the flare tube 1930 beyond the capability of the core, providing increased control over customization of the implant. FIG. 19B illustrates a proximal facing perspective view of a core 2000, having a plurality of flanges 2020a-2020h. A balloon 2025 is shown disposed within a lumen of the core. As the balloon 2025 inflates, pressure may be applied radially outward upon flanges 2020a-2020h in a direction generally indicated by arrows 2030a-2030d. As shown in FIG. 19B, the individual pressure applied to each arm will vary based on the shape of the balloon such that asymmetrical balloons may be used to customize implant shape and deployment.

Balloons may be used to control expansion of the frame using flare tubes in a variety of embodiments. For example, a balloon may be disposed within a unified core that does not include independently controllable arms, may be disposed within a core including arms that translate in unison or individually, or may be disposed directly within the sleeve, without use of a core.

Accordingly, numerous embodiments of systems and method of use of an implant deployment comprising removable actuators have been shown and described. It should be noted that although the particularly disclosed embodiments include an expandable frame, the invention is not limited to use with implants having an expandable frame, but rather it is appreciated may be used with other forms of implants. Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination. Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An implant delivery system comprising:
a frame having a proximal end, a distal end, and adjacent struts joined at a proximal apex;
a collar disposed over at least one proximal apex; and
a shaft operatively coupled with the at least one proximal apex of the frame;
wherein:
axial translation of the collar over the at least one proximal apex adjusts the relative positions of the adjacent struts joined at the at least one proximal apex to expand or contract the frame; and
the collar is disposed over and operatively engages at least a portion of the shaft and is configured to travel axially along the shaft and over and around the at least one proximal apex of the frame to engage the adjacent struts joined at the at least one proximal apex to adjust the positions of the adjacent struts to expand or contract the frame in response to a first activation of the shaft.

2. The implant delivery system of claim 1, wherein:
the shaft has a distal shaft end comprising a shaft head positioned within an opening of the at least one proximal apex of the frame, a proximal shaft end comprising a drive coupler, and shaft engagement features disposed along a portion of an engagement portion of the shaft disposed between the drive coupler and the shaft head;
the collar has a proximal end, a distal end, and a bore extending therethrough, the bore comprising bore engagement features disposed on at least a portion of an inner surface of the bore;
the shaft engagement features are configured to engage with the bore engagement features to axially translate the collar along the shaft and over and around the at least one proximal apex to expand or contract the frame;
the collar is disposed over at least a portion of the shaft head to retain the shaft head within the opening of the at least one proximal apex; and
the collar is configured to travel proximally along the shaft in response to a second activation of the shaft to release the shaft head from the proximal end of the frame.

3. The implant delivery system of claim 2, wherein a length of the engagement portion of the shaft is at least equal to a length of the collar.

4. The implant delivery system of claim 2, wherein:
at least one of the shaft engagement features or the bore engagement features includes one or more threads; and
one of the first activation or the second activation of the shaft includes rotation of the shaft.

5. The implant delivery system of claim 1, wherein:
adjacent struts of the frame are joined at a distal apex the distal apex supports an anchor housing; and
the anchor housing comprises a cinch lumen extending therethrough configured to slidably accept a cinch cord.

6. The implant delivery system of claim 1, wherein adjacent struts include a biased configuration, and wherein the collar includes a spreading mechanism configured to urge the adjacent struts against returning to the biased configuration.

7. The implant delivery system of claim 6, wherein the spreading mechanism includes at least one arm configured to engage at least one strut of the adjacent struts to urge the at least one strut against returning to the biased configuration.

8. The implant delivery system of claim 7, wherein release of the shaft from the at least one proximal apex releases the spreading mechanism from between the adjacent struts to return the adjacent struts to the biased configuration.

9. An implant delivery system comprising:
a frame having a proximal end, a distal end, and adjacent struts joined at a proximal apex; and
a collar disposed over at least one proximal apex; and
an actuator;
wherein:
the frame further includes a plurality of distal apices and a plurality of anchor housings disposed on at least a subset of the plurality of distal apices, each anchor housing supporting an anchor;
the actuator includes:
a sleeve;
a plurality of cantilevered tubes disposed within the sleeve and coupled at proximal ends to a distal portion of the sleeve;
a plurality of drive shafts, each drive shaft translatably disposed within one of the plurality of cantilevered tubes and configured to extend beyond the distal end of an associated cantilevered tube to drive one of the anchors; and
a core disposed within the sleeve such that the plurality of cantilevered tubes slideably engage an outer surface of the core, the core disposed to translate axially within the sleeve, wherein each cantilevered tube includes a flex portion, and wherein axial translation of the core causes the cantilevered tubes to rotate at the flex portion to vary an angular deflection of the distal end of the cantilevered tube to expand the distal apices of the frame; and
axial translation of the collar over the at least one proximal apex adjusts the relative positions of the adjacent struts joined at the at least one proximal apex to expand or contract the frame.

10. The implant delivery system of claim 9, wherein the core includes a plurality of arms arranged circumferentially within the sleeve, and wherein the plurality of arms is independently translatable within the sleeve to independently control the angular deflection of a respective cantilevered tube.

11. The implant delivery system of claim 10, wherein each drive shaft is axially translatable beyond a distal end of an associated cantilevered tube to control a configuration of the frame.

12. The implant delivery system of claim 11, further comprising an inflatable device, disposed within a central lumen of the core and configured to control an angular deflection of the plurality of cantilevered tubes.

13. The implant delivery system of claim 12, wherein the core includes a plurality of detents, each detent for slidably supporting one of the plurality of cantilevered tubes.

14. A system comprising:
a catheter;
a frame having a proximal end, a distal end, and a plurality of adjacent struts joined at a plurality of respective distal apices and a plurality of respective proximal apices;
one or more anchors each supported by a respective distal apex of the frame and having a proximal anchor head comprising a drive coupling configured to be engaged by a drive shaft configured to drive the anchor into tissue; and
one or more axially translatable adjustment components configured for one of expansion or contraction of the frame and configured for removal through the catheter following affixation of the frame by the plurality of anchors into tissue;
wherein:
the one or more axially translatable adjustment components includes:
a shaft having a distal shaft end comprising a shaft head, the shaft head positioned within an opening of a proximal apex of the frame; and
a collar disposed over at least a portion of the shaft to retain the shaft head within the opening of the proximal apex, the collar configured to travel distally along the shaft and over a proximal apex of one of the plurality of proximal apices of the frame to engage the adjacent struts to one of expand or compress the frame in response to a first activation of the shaft; and
the collar is configured to travel proximally along the shaft in response to a second activation of the shaft to release the shaft head from the proximal apex of the frame.

15. The system of claim 14, wherein the one or more axially translatable adjustment components includes:
- a sleeve;
- a plurality of cantilevered tubes disposed within the sleeve and coupled at proximal ends to a distal portion of the sleeve;
- a plurality of drive shafts, each drive shaft translatably disposed within one of the plurality of cantilevered tubes and configured to extend beyond the distal end of an associated cantilevered tube to drive one of the anchors into tissue; and
- a core disposed within the sleeve such that the plurality of cantilevered tubes slideably engage an outer surface of the core, the core disposed to translate axially within the sleeve, wherein each cantilevered tube includes a flex portion, and wherein axial translation of the core causes the cantilevered tubes to rotate at the flex portion to vary an angular deflection of the distal end of the cantilevered tube drive shafts to expand the distal apices of the frame.

* * * * *